(12) United States Patent
Ding et al.

(10) Patent No.: US 11,260,390 B2
(45) Date of Patent: Mar. 1, 2022

(54) LATERAL-FLOW ASSAY DEVICE HAVING FLOW CONSTRICTIONS

(71) Applicant: ORTHO-CLINICAL DIAGNOSTICS, INC., Raritan, NJ (US)

(72) Inventors: Zhong Ding, Pittsford, NY (US); Edward R. Scalice, Penfield, NY (US); Daniel P. Salotto, Rochester, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 523 days.

(21) Appl. No.: 16/054,024

(22) Filed: Aug. 3, 2018

(65) Prior Publication Data
US 2018/0345277 A1    Dec. 6, 2018

Related U.S. Application Data

(62) Division of application No. 14/817,760, filed on Aug. 4, 2015, now Pat. No. 10,071,373.
(Continued)

(51) Int. Cl.
*G01N 33/543* (2006.01)
*B01L 3/00* (2006.01)

(52) U.S. Cl.
CPC ...... *B01L 3/5023* (2013.01); *G01N 33/54386* (2013.01); *B01L 2300/041* (2013.01);
(Continued)

(58) Field of Classification Search
CPC ....... B01L 2300/041; B01L 2300/0867; B01L 2300/161; B01L 2400/0406; B01L 3/5023; G01N 33/54386
See application file for complete search history.

(56) References Cited

U.S. PATENT DOCUMENTS

| 4,287,155 A | 9/1981 | Tersteeg et al. |
| 5,120,643 A | 6/1992 | Ching et al. |

(Continued)

FOREIGN PATENT DOCUMENTS

| EP | 0920356 | 12/2002 |
| EP | 1292449 | 10/2008 |

(Continued)

OTHER PUBLICATIONS

Sematand Katz (1958) Physics, Ch 9: Hydrodynamics, Robert Katz Productions. (Year: 1958).*

(Continued)

*Primary Examiner* — Rebecca M Giere
(74) *Attorney, Agent, or Firm* — K&L Gates LLP; Louis C. Cullman; Brian J. Novak

(57) ABSTRACT

A lateral-flow assay device includes a substrate having a sample addition zone and a wash addition zone downstream thereof along a fluid flow path through which a sample flows. The fluid flow path is configured to receive a wash fluid in the wash addition zone. A hydrophilic surface is arranged in the wash addition zone. Flow constriction(s) are spaced apart from the fluid flow path and arranged to define, with the hydrophilic surface, a reservoir configured to retain the wash fluid by formation of a meniscus between the hydrophilic surface and the flow constriction(s). The fluid flow path draws the wash fluid from the reservoir by capillary pressure. Apparatus for analyzing a fluidic sample and methods of displacing a fluidic sample in a fluid flow path of an assay device are also described.

10 Claims, 15 Drawing Sheets

Related U.S. Application Data

(60) Provisional application No. 62/034,825, filed on Aug. 8, 2014.

(52) U.S. Cl.
CPC . *B01L 2300/0867* (2013.01); *B01L 2300/161* (2013.01); *B01L 2400/0406* (2013.01)

(56) References Cited

U.S. PATENT DOCUMENTS

| | | |
|---|---|---|
| 5,559,041 A | 9/1996 | Kang et al. |
| 5,607,863 A | 3/1997 | Chandler |
| 5,714,389 A | 2/1998 | Charlton et al. |
| 5,869,004 A | 2/1999 | Parce et al. |
| 6,048,498 A | 4/2000 | Kennedy |
| 6,139,800 A | 10/2000 | Chandler |
| 6,228,660 B1 | 5/2001 | May et al. |
| 6,241,886 B1 | 6/2001 | Kitagawa et al. |
| 6,270,641 B1 | 8/2001 | Griffiths et al. |
| 6,372,542 B1 | 4/2002 | Martin et al. |
| 6,402,300 B1 | 6/2002 | Silverbrook |
| 6,451,264 B1 | 9/2002 | Bhullar et al. |
| 6,733,682 B1 | 5/2004 | Bjoerkman et al. |
| 6,776,965 B2 | 8/2004 | Wyzgol et al. |
| 6,811,736 B1 | 11/2004 | Ohman et al. |
| 6,884,370 B2 | 4/2005 | Ohman et al. |
| 6,896,358 B1 | 5/2005 | Silverbrook |
| 7,005,301 B2 | 2/2006 | Cummings et al. |
| 7,032,992 B2 | 4/2006 | Silverbrook |
| 7,132,078 B2 | 11/2006 | Rawson et al. |
| RE39,664 E | 5/2007 | Gordon et al. |
| 7,267,423 B2 | 9/2007 | Silverbrook |
| 7,312,084 B2 | 12/2007 | Jakubowicz et al. |
| 7,416,700 B2 | 8/2008 | Buechler et al. |
| 7,503,954 B2 | 3/2009 | Haefner et al. |
| 7,581,817 B2 | 9/2009 | Silverbrook |
| 7,632,468 B2 | 12/2009 | Barski et al. |
| 7,654,643 B2 | 2/2010 | Silvebrook |
| 7,816,122 B2 | 10/2010 | Clark et al. |
| 7,819,507 B2 | 10/2010 | Brown et al. |
| 7,883,183 B2 | 2/2011 | Silverbrook |
| 7,891,769 B2 | 2/2011 | Silverbrook |
| 7,984,968 B2 | 7/2011 | Silverbrook |
| 8,025,854 B2 | 9/2011 | Ohman et al. |
| 8,043,562 B2 | 10/2011 | Tomasso et al. |
| 8,080,204 B2 | 12/2011 | Ryan et al. |
| 8,821,812 B2 | 9/2014 | Ohman et al. |
| 10,712,340 B2 * | 7/2020 | Scalice ............... G01N 33/5302 |
| 2004/0072367 A1 | 4/2004 | Ding et al. |
| 2005/0116990 A1 | 6/2005 | Silverbrook |
| 2006/0205086 A1 | 9/2006 | Hu |
| 2006/0239859 A1 | 10/2006 | Ohman et al. |
| 2006/0289787 A1 | 12/2006 | Ohman et al. |
| 2007/0231883 A1 | 10/2007 | Lindstrom et al. |
| 2007/0268328 A1 | 11/2007 | Silverbrook |
| 2008/0176272 A1 | 7/2008 | Bergman et al. |
| 2009/0047691 A1 * | 2/2009 | Huwig ............. G01N 33/56944 435/7.34 |
| 2009/0068061 A1 | 3/2009 | Chen |
| 2010/0176050 A1 | 7/2010 | Mori |
| 2011/0011781 A1 | 1/2011 | Blankenstein et al. |
| 2011/0053289 A1 | 3/2011 | Lowe et al. |
| 2013/0189672 A1 | 7/2013 | Ding |
| 2013/0189673 A1 * | 7/2013 | Scalice ............... G01N 33/5302 435/5 |
| 2013/0330713 A1 | 12/2013 | Jakubowicz et al. |
| 2014/0141527 A1 | 5/2014 | Ding et al. |
| 2014/0220606 A1 * | 8/2014 | Puntambekar ........ B01L 3/5025 435/7.94 |

FOREIGN PATENT DOCUMENTS

| | | |
|---|---|---|
| WO | WO9932884 | 7/1999 |
| WO | WO03103835 | 12/2003 |
| WO | WO2005089082 | 9/2005 |
| WO | WO2005118139 | 12/2005 |
| WO | WO2006137785 | 12/2006 |
| WO | WO20071490042 | 12/2007 |
| WO | WO2012123751 | 9/2012 |
| WO | WO2014114949 | 7/2014 |

OTHER PUBLICATIONS

Chinese Office Action issued in related Chinese Patent Application No. 201580054321.2 dated Mar. 15, 2018 and English translation of same.

A. Nabatiyan, "Membrane-based plasma collection device for point-of-care diagnosis of HIV," Journal of Virological Methods, vol. 173, No. 1, Jan. 2011, pp. 37-42.

International Search Report and Written Opinion for PCT/US2015/043757, dated Nov. 18, 2015; 9 pages.

* cited by examiner

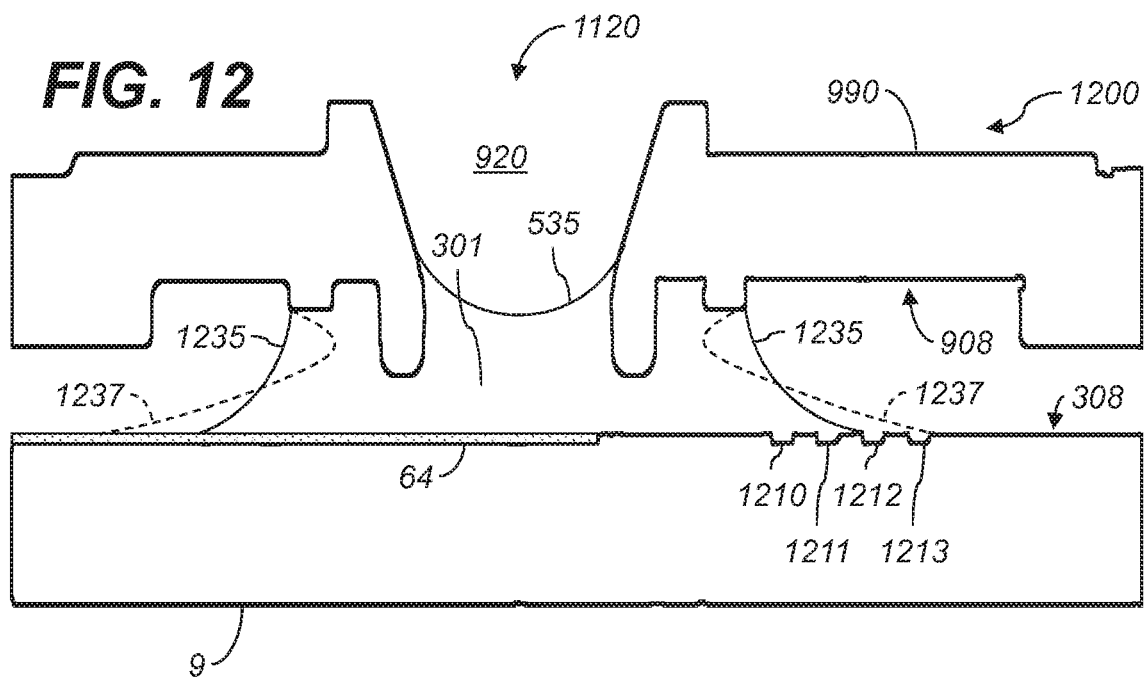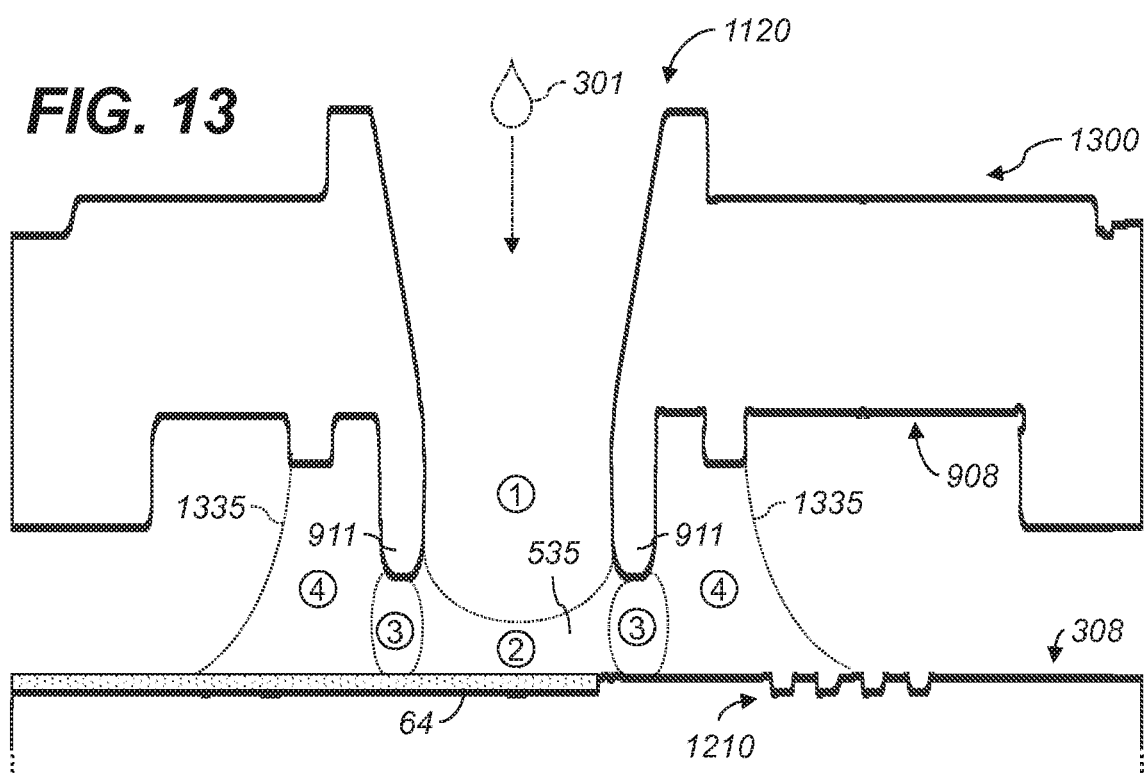

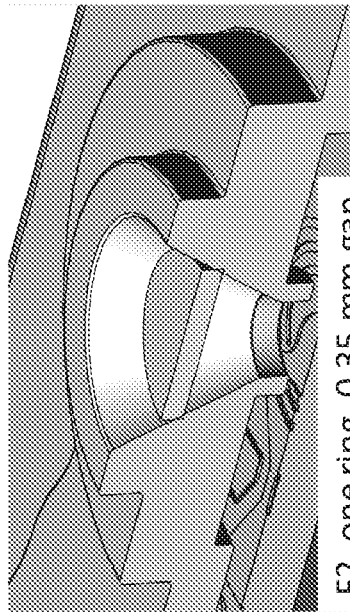
FIG. 15 F1, one ring, 0.75 mm gap
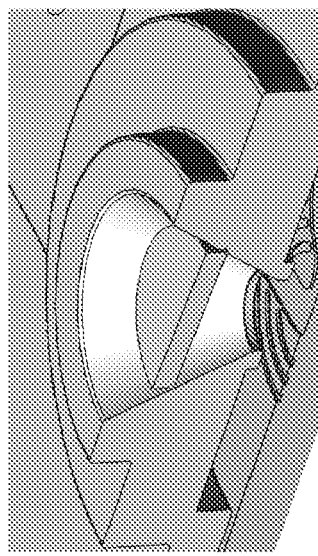
FIG. 16 F2, one ring, 0.35 mm gap
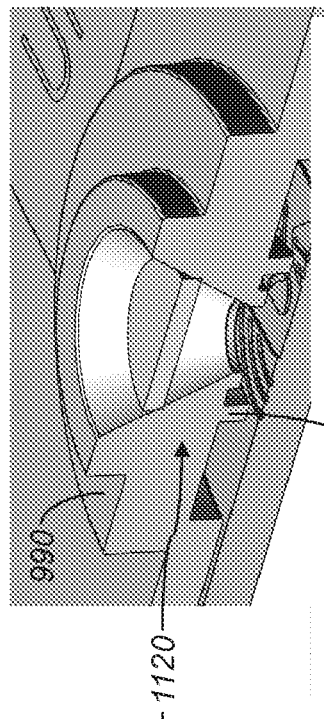
FIG. 17 F3, two rings, 0.35 mm gap
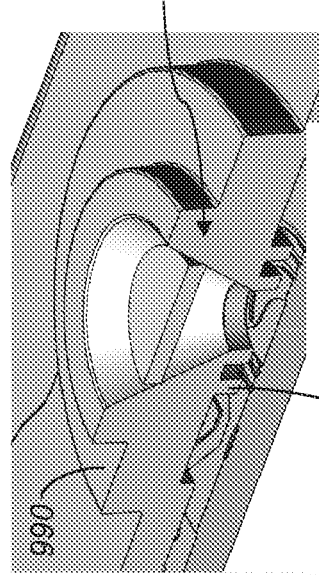
FIG. 18 F4, two rings, inner 0.75, outer 0.35 mm

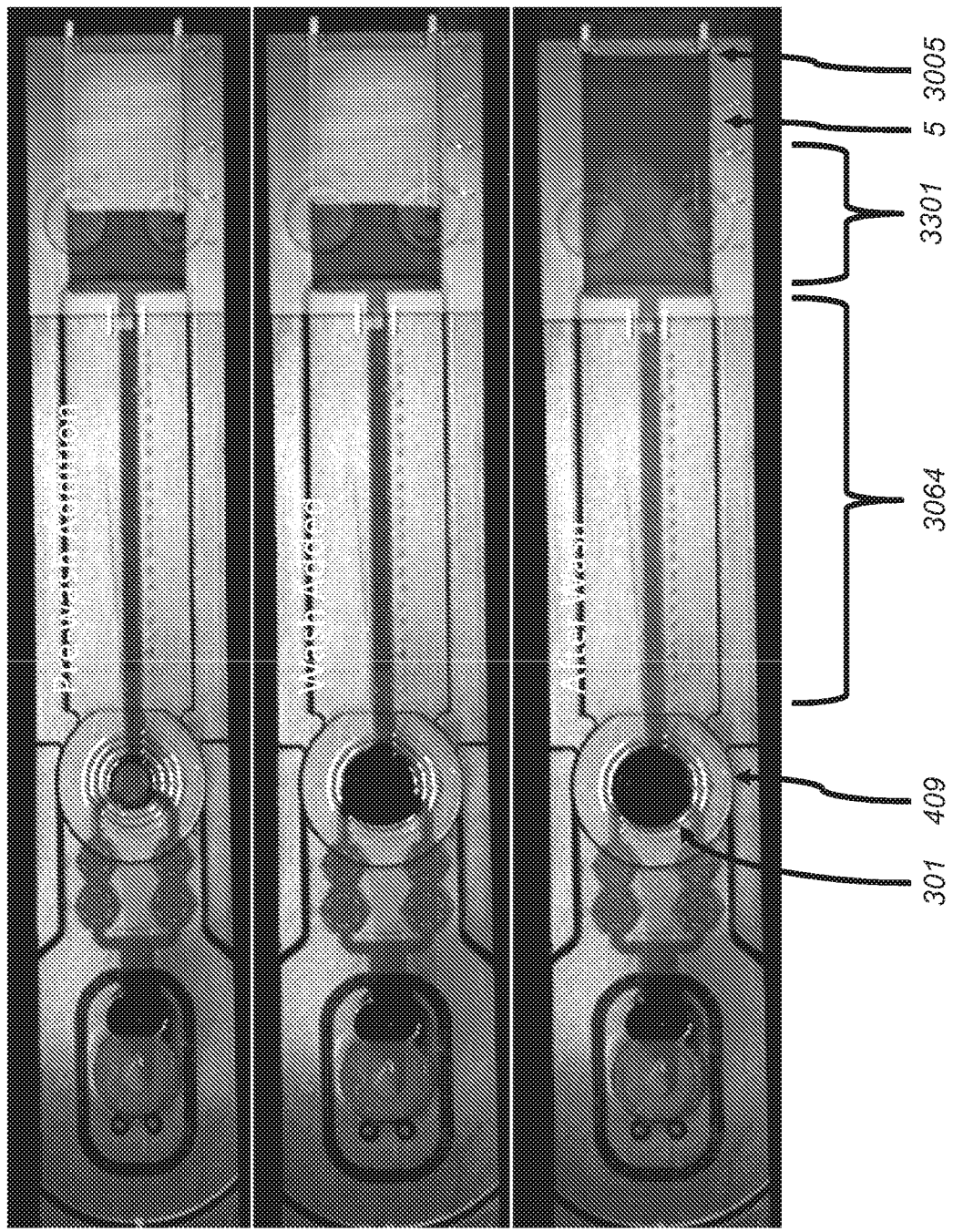

LATERAL-FLOW ASSAY DEVICE HAVING FLOW CONSTRICTIONS

CROSS REFERENCE TO RELATED APPLICATION(S)

This application claims priority to and the benefit as a divisional application of U.S. patent application Ser. No. 14/817,760, filed Aug. 4, 2015 and entitled: LATERAL-FLOW ASSAY DEVICE HAVING FLOW CONSTRICTIONS, which claims priority under applicable portions of 35 U.S.C. § 119 to U.S. patent application Ser. No. 62/034,825, filed Aug. 8, 2014 and entitled: LATERAL-FLOW ASSAY DEVICE HAVING FLOW CONSTRICTIONS, the entire contents of each of which are herein incorporated by reference.

TECHNICAL FIELD

This application relates to the field of clinical diagnostics and more specifically to lateral-flow assay devices.

BACKGROUND

The use of diagnostic assays is very well known for the diagnosis, treatment and management of many diseases. In that regard, different types of diagnostic assays have been developed to simplify the detection of various analytes in clinical samples such as blood, serum, plasma, urine, saliva, tissue biopsies, stool, sputum, skin or throat swabs and tissue samples or processed tissue samples. These assays are frequently expected to provide a fast and reliable result, while being easy to use and inexpensive to manufacture, One common type of disposable assay device includes a sample addition zone or area for receiving the liquid sample, at least one reagent zone (also known as a conjugate zone), a reaction zone (also known as a detection zone), and optionally an absorbing zone. These zones can be arranged in order along a fluid passage or channel. These assay devices, commonly known as lateral test strips, can employ a porous material, e.g., nitrocellulose, defining a path for fluid capable of supporting capillary flow. Examples include those devices shown in U.S. Pat. Nos. 5,559,041, 5,714,389, 5,120,643, and 6,228,660, all of which are incorporated herein by reference in their entireties.

The sample addition zone of these assay devices frequently includes a porous material, capable of absorbing the liquid sample, and, when separation of blood cells is required, also effective to trap the red blood cells. Examples of such materials are polymeric membrane filters or fibrous materials, such as paper, fleece, or tissue, comprising e.g., cellulose, wool, glass fiber, asbestos, synthetic fibers, polymers, or mixtures of the same, Another type of lateral-flow assay device is defined by a non-porous substrate having a plurality of upwardly extending microposts (also referred to as "micropillars" or "projections"). The microposts are defined dimensionally and in terms of their spacing to produce capillary flow when a liquid is introduced. Examples of such devices are disclosed in U.S. Pat. No. 8,025,854B2, WO 2003/103835, WO 2005/089082, WO 2005/118139 and WO 2006/137785, all of which are incorporated by reference herein in their entireties, A known non-porous assay device of the above type is shown in FIG. 1. The lateral-flow assay device 1 has at least one sample addition zone 2 configured to receive a sample 101, graphically represented using a teardrop shape. The sample 101 can include, e.g., a bodily fluid or other fluid to be tested for an analyte. The lateral-flow assay device 1 also includes a reagent zone 3, at least one detection zone 4, and at least one wicking zone 5, each disposed on a common substrate 9. The zones 2, 3, 4, 5 are aligned along a defined fluid flow path 64 by which the sample 101 or a portion thereof flows from the sample addition zone 2 to the wicking zone 5 under the influence of capillary pressure provided between ones of a -plurality of microposts 7. Capture elements, such as antibodies, can be supported in the detection zone 4, these elements being capable of binding to an analyte of interest, the capture elements being deposited on the device, e.g., by coating. The term "element" is not limited to atoms, i.e., chemical elements of the periodic table, but can also refer to molecules, e.g., of ionically or covalently-bonded atoms, or other chemical compounds or biological substances. In addition, a labeled conjugate material, also capable of participating in reactions that will enable determination of the concentration of the analyte, is separately deposited on the device in the reagent zone 3, wherein the conjugate material carries a label for detection in the detection zone 4 of the lateral-flow assay device 1.

The conjugate material is gradually dissolved as the sample 101 flows through the reagent zone 3, forming a conjugate plume of dissolved labeled conjugate material and sample 101 that flows downstream along the defined fluid flow path 64 of the lateral-flow assay device 1 to the detection zone 4, As the conjugate plume flows into the detection zone 4, the conjugated material will be captured by the capture elements such as via a complex of conjugated material and analyte (e.g., as in a "sandwich" assay) or directly (e.g., as in a "competitive" assay). Unbound dissolved conjugate material will be swept past the detection zone 4 and into the wicking zone 5.

An instrument such as that disclosed in U.S. 2006/0289787A1, U.S. 2007/0231883A1, U.S. Pat. Nos. 7,416,700 and 6,139,800, all incorporated by reference in their entireties herein, is configured to detect the bound conjugated material in the detection zone 4. Common labels include fluorescent dyes that can be detected by instruments which excite the fluorescent dyes and incorporate a detector capable of detecting the resulting fluorescence. In the foregoing devices and in the conduction of assays, the resulting level of signal in the detection zone is read using a suitable detection instrument after the conjugate material has been dissolved and the sample 101 and unbound conjugate material have reached and subsequently filled the wicking zone 5 of the lateral-flow assay device 1.

In a typical point of care (POC) lateral flow assay format, it is desirable to remove unbound conjugate materials to lower background signal and improve assay accuracy. In some assays, fluid of the sample 101 continues to flow through the detection zone 4 after all the dissolved conjugate passes the detection zone 4. In this way, the flowing sample 101 removes unbound conjugate materials. However, endogenous interferents may be present in the sample 101 that may interfere with assay results (e.g., hemoglobin, bilirubin of a particular patient). For these assays, wash fluid separate from the sample 101 can be applied to remove the interferent from the detection zone 4 or other parts of the detection channel. Moreover, some assays involve pre-mixing the conjugate material with the sample 101 prior to addition of the mix to the sample addition zone 2 to obtain a longer incubation time. For these types of assays, since the sample 101 is mixed with the conjugate, a wash fluid is applied to remove unbound conjugate from the detection zone 4. In these and other embodiments, wash fluid can be formatted or designed to provide an acceptable wash. Accordingly, adding wash fluid is necessary for some selected assays in, e.g., a POC lateral flow format.

However, adding wash reagent is a challenge in various prior lateral-flow assay devices. The wash fluid is to flow in the gaps between pillars (or in the pores of a porous structure, such as cellulose acetate). However, since flow resistance in gaps or pores is much larger than outside of the pillar matrix (or porous) structure, wash fluid cannot be "pushed" into the fluid flow path 64 (the pillar matrix) to accomplish the wash. Wash fluid has to be "pulled" into the gaps between pillars or pores of a porous material by the capillary pressure. There is therefore a need for assay devices and ways of using assay devices that are more compatible and usable with various wash fluids.

BRIEF DESCRIPTION

According to one aspect, there is provided a lateral-flow assay device comprising:

a) a substrate having a sample addition zone and a wash addition zone disposed along a fluid flow path through which a sample flows under capillary action in a downstream direction away from the sample addition zone and towards the wash addition zone, wherein the fluid flow path is configured to receive a wash fluid in the wash addition zone;

b) at least one hydrophilic surface arranged in the wash addition zone; and c) one or more flow constriction(s) spaced apart from the fluid flow path and arranged to define, with the at least one hydrophilic surface, a reservoir configured to retain the wash fluid by formation of a meniscus between the hydrophilic surface and the one or more flow constriction(s); wherein the fluid flow path is configured to draw the wash fluid from the reservoir by capillary pressure.

According to another aspect, there is provided apparatus for analyzing a fluidic sample, the apparatus comprising:

a) at least one assay device including a sample addition zone and a wash addition zone disposed along a fluid flow path;

b) a sample-metering mechanism configured to selectively apply the fluidic sample to the sample addition zone;

c) a wash-metering mechanism configured to selectively apply a wash fluid to the wash addition zone, wherein the wash addition zone includes one or more flow constriction(s) spaced apart from the fluid flow path to form a meniscus in the applied wash fluid;

d) at least one measurement device; and e) a controller configured to operate each of the sample-metering mechanism, wash-metering mechanism, and at least one measurement device in accordance with a predetermined timing protocol in order to determine at least one characteristic of the applied fluidic sample, wherein the controller operates the wash-metering mechanism after operating the sample-metering mechanism.

According to still another aspect, there is provided a method of displacing a fluidic sample in a fluid flow path of an assay device, the method comprising:

dispensing the fluidic sample from a sample supply onto a sample addition zone of the assay device, wherein the dispensed fluidic sample travels along the fluid flow path of the assay device; and dispensing a wash fluid from a wash-fluid supply onto a wash addition zone of the assay device downstream of the sample addition zone along the fluid flow path so that a meniscus is formed in the dispensed wash fluid by at least one flow constriction of the assay device, wherein the fluid-flow path draws dispensed wash fluid out of a reservoir defined at least partly by the meniscus and the drawn wash fluid displaces at least some of the fluidic sample in the fluid-flow path.

Various aspects advantageously provide an effective supply of the wash fluid to the fluid flow path, even in the face of variations in the rate of wash-fluid delivery or the volume of wash fluid delivered. Various aspects advantageously restrict the wash fluid from flowing outside the pillar (or other porous) structures of the fluid flow path. Various aspects advantageously effectively restrict the flow of the sample through the fluid flow path, which can improve the accuracy of assays.

These and other features and advantages of various embodiments, variations, and modifications will be readily apparent from the following Detailed Description, Which should be read in conjunction with the accompanying drawings.

BRIEF DESCRIPTION OF THE DRAWINGS

FIG. 12 is an elevational section of an exemplary lateral-flow assay device illustrating effects of contact angle;

FIG. 13 is an elevational section of an exemplary lateral-flow assay device illustrating stages in which fluid fills an internal volume of the lateral-flow assay device;

FIGS. 15-27 are perspectives of components of lateral-flow assay devices according to various aspects;

FIGS. 31-33 are graphical representations of photographs of stages in another experimental test of an exemplary lateral-flow assay device according to various aspects;

DETAILED DESCRIPTION

Figure 1:
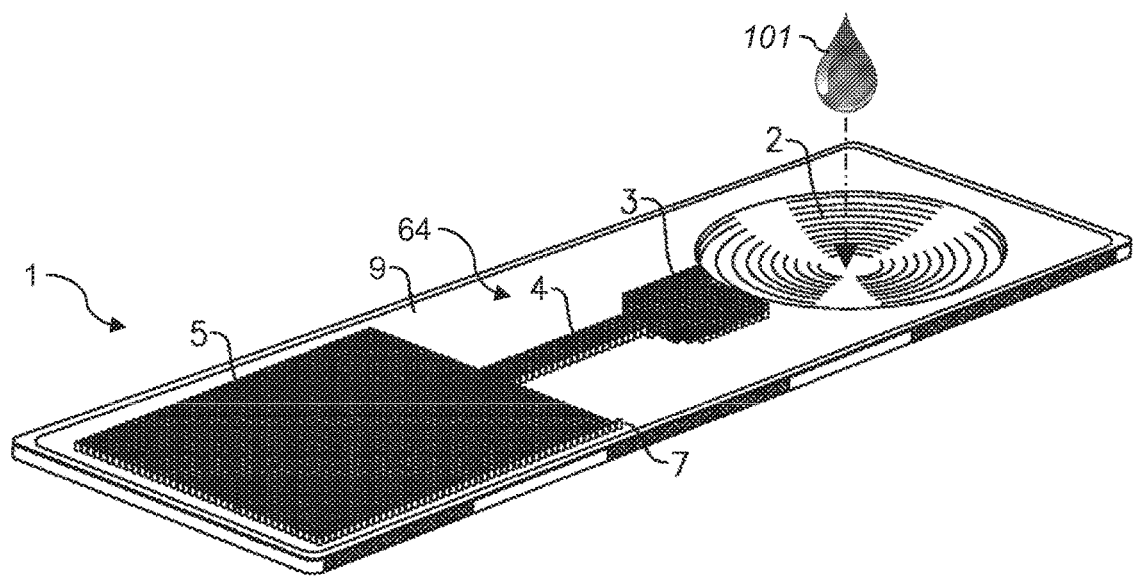
FIG. 1 is a perspective view of a known lateral-flow assay device.

The following description relates to certain embodiments for a wash addition area design for a lateral-flow assay device. It will be readily apparent that the embodiments described herein are intended to be merely exemplary and therefore numerous other variations and modifications are possible. In addition, several terms are used throughout the following discussion such as "first", "second"; "above" "below", "top", "bottom", "lateral" and the like for purposes of providing a suitable frame of reference in regard to the accompanying drawings. To that end, these terms should not be regarded as being overly restrictive in terms of the scope of the described. apparatus and methods, unless otherwise specifically indicated herein.

It should further be noted that the accompanying drawings are not necessarily presented to scale and therefore no narrowing interpretation should be made in terms of dimensions that have been depicted.

As used in this specification and the appended claims, the singular forms "a", "an" and "the" are intended to further include plural referents unless the context clearly dictates otherwise.

The term "about" as used in connection with a numerical value throughout the description and the claims denotes an interval of accuracy, familiar and acceptable to a person skilled in the art. The interval governing this term is preferably ±30%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" herein means a volume of a liquid, solution or suspension, intended to be subjected to qualitative or quantitative determination of any of its properties, such as the presence or absence of a component, the concentration of a component, etc. Typical samples in the context of the present invention as described herein are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This represents only a small example of samples that can be used in the present invention.

As described herein, determinations based on lateral flow of a sample and the interaction of components present in the sample with reagents present in the device or added to the device during the procedure, and detection Of such interaction, either quantitatively or qualitatively, may be for any purpose, such as diagnostic purposes. Such tests are often referred to as "lateral flow assays".

Examples of diagnostic determinations include, but are not limited to, the determination of analytes, also called markers, specific for different disorders, e.g., chronic metabolic disorders, such as blood glucose, blood ketones, urine glucose (diabetes), blood cholesterol (atherosclerosis, obesity, etc.); markers of other specific diseases., e.g., acute diseases, such as cardiac coronary infarct markers (e.g., troponin I, troponin-T, NT-proBNP), markers of thyroid function (e.g., determination of thyroid stimulating hormone (TSH)), markers of viral infections (e.g., the use of lateral flow immunoassays for the detection of specific viral antibodies), etc.

Yet another important field of assays is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, assay devices as described herein can be used prior to administration of a therapeutic agent to determine if the agent will help the individual in need.

Yet another important field of assays is that of drug tests, for easy and rapid detection of drugs and drug metabolites indicating drug abuse. Exemplary assays include the determination of specific drugs and drug metabolites in a urine or other sample.

The term "lateral-flow assay device", as discussed herein, refers to any device that receives fluid, such as at least one sample, such as a bodily fluid sample, and includes at least one laterally disposed fluid transport or flow path along which various stations or sites (zones) are provided for supporting various reagents, filters and the like through which sample traverses under the influence of capillary or other applied forces and in which lateral flow assays are conducted for the detection of at least one analyte of interest.

The terms "automated clinical analyzer", "clinical diagnostic apparatus" or "clinical analyzer," as discussed herein, refer to any apparatus enabling the scheduling and processing of various analytical test elements, including lateral-flow assay devices, as discussed herein, and in which a plurality of test elements can be initially loaded for processing. Such apparatus can include a plurality of components or systems configured for loading, incubating and testing/evaluating a plurality of analytical test elements in automated or semi-automated fashion and in which test elements are automatically dispensed from at least one contained storage supply, such as a cartridge, without user intervention.

The term "testing apparatus" refers to any device or analytical system that enables the support, scheduling and processing of lateral-flow assay devices. A testing apparatus can include an automated clinical analyzer or clinical diagnostic apparatus such as a bench, table-top or main frame clinical analyzer, as well as point of care and other suitable devices. For purposes of this application, the testing apparatus may include a plurality of components or systems for loading, testing, or evaluating at least one lateral-flow assay device, including detection instruments for detecting the presence of at least one detectable signal of the assay device.

The terms "zone", "area" and "site" are interchangeably used in the context of this description, examples and claims to define parts of a fluid flow path on an assay device, either in prior art devices or according to an embodiment described herein, including devices in which a sample is first applied to the device and then subsequently directed. The term "reaction" is used to refer to any interaction that takes place between components of a sample and reagent(s) on or in the substrate, or between two or more components present in the sample. The term "reaction" is in particular used to define a reaction taking place between an analyte and a reagent as part of the qualitative or quantitative determination of the analyte.

The terms "substrate" or "support" refers to the carrier or matrix to which a sample is added, and on or in which the determination is performed, or where the reaction between analyte and reagent takes place.

The term "detection" and "detection signal" refers herein to the ability to provide a perceivable indicator that can be monitored either visually and/or by machine vision such as a detection instrument (e.g., a fluorimeter, reflectometer or other suitable device)

Figure 2:
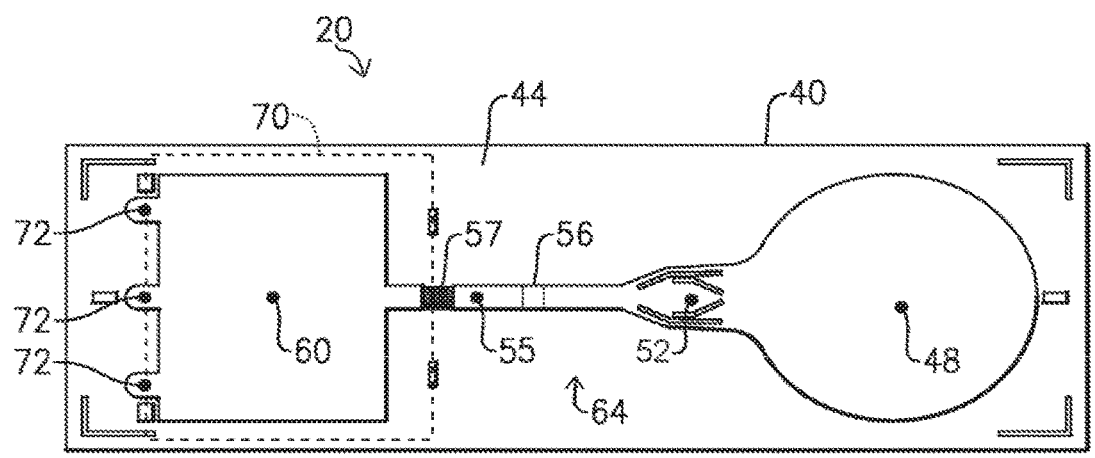
FIG. 2 is a plan view of another known lateral-flow assay device.

Referring to FIG. 2, there is shown one version of a lateral-flow assay device 20 including a planar substrate 40 which can be made from a moldable plastic or other suitable non-porous material. Further details of this and related devices are described below and in U.S. Patent Application Publication No. 2014/0141527 A1, entitled "Quality/Process Control of a Lateral-flow assay device Based on Flow Monitoring," which is incorporated herein by reference in its entirety.

The substrate 40 is defined by a top surface 44, which is further defined by a fluid flow path 64. The fluid flow path 64 includes a plurality of discrete areas or zones in spaced relation to one another including a sample addition zone 48, a reagent zone 52, a plurality of detection zones 56 located in a detection channel 55 (for clarity, only one detection zone 56 is shown) and a receiving or wicking zone 60. According to this design, each of the above-noted. zones are fluidly interconnected with one another in linear fashion along at least one defined fluid flow path 64 and in which a plurality of microposts 7, FIG. 1, are disposed within at least one of the zones and/or the fluid flow path 64, the microposts 7 extending upwardly from either the lower surface of the fluid flow path 64 or the discrete zones defined on the lateral-flow assay device 20.

The microposts 7 are preferably dimensioned to induce lateral capillary flow, wherein the microposts 7 preferably include a height, diameter and/or center to center spacing to induce fluidic flow along the at least one fluid flow path. In one version thereof, the microposts 7 can be sufficiently dimensioned so as to induce capillary flow as a so-called "open" structure without the need for additional structure (i.e., side walls, cover or lid) or the application of any externally applied forces. According to this specific design, a defined fluid flow path 64 is created, extending from the sample addition zone 48 to the wicking zone 60. The illustrated fluid flow path 64 extends substantially in a straight-line fashion between the sample addition zone 48 and the wicking zone 60. In other configurations, the fluid flow path 64 can include one or more lateral bends or turns.

As noted and in various embodiments, the defined fluid flow path 64 is at least partially open, or entirely open. As noted above and by "open" what is meant is that there is no lid or cover which is maintained at a distance that would contribute to capillary flow. Thus a lid, if present as physical protection for the fluid flow path 64 and the lateral-flow assay device 20, is not required to contribute to the capillary flow in the flow path. According to this specific design, a hydrophilic layer 70 can be directly applied to the top of the microposts 7 in the wicking zone 60 in order to increase fluid flow in the lateral-flow assay device 20 and in which a plurality of vents 72 can be defined in the hydrophilic layer 70. The hydrophilic layer 70 can include a plastic backer tape (not shown) and a hydrophilic adhesive (not shown) on the side of the hacker tape arranged to face the fluid flow path 64. In various examples, a flow promoter 57 is arranged in the fluid flow path 64 bridging the edge of the hydrophilic layer 70 to promote flow under the hydrophilic layer 70 placed over the wicking zone 60.

Various examples of flow promoters, mixers, flow restrictors, and other structures useful for controlling flow in the fluid flow path 64 are described in U.S. patent application Ser. No. 62/035,083, filed Aug. 8, 2014, the disclosure of which is incorporated herein by reference in its entirety. That application describes examples of size and shape characteristics of the sample addition zones 48 according to various aspects, features in the reagent zone 52 to effect more efficient dissolution according to various aspects, a curved portion of the fluid flow path 64 configured to mix fluid passing through the fluid flow path 64 according to various aspects, and features in the wicking zone 60 including flow promoters similar to the flow promoter 57 according to various aspects.

An open lateral flow path is described including the defined microposts 7, for example, in the following published applications: WO 2003/103835, WO 2005/089082; WO 2005/118139; WO 2006/137785; and WO 2007/149042, all of which are incorporated by reference in their entireties. The extending microposts 7 have a height, diameter and a distance or distances between the microposts 7 such that lateral capillary flow of an applied fluid, such as plasma, preferably human plasma, in the zone having the microposts 7 is achieved. These relationships are discussed in U.S. Pat. No. 8,821,812, which is incorporated by reference in its entirety.

In addition to optimizing the above-mentioned height, diameter and a distance or distances, the above-noted microposts 7 may be given a desired chemical, biological or physical functionality, e.g. by modifying the surface of the microposts 7 for purposes, for example, of the reagent zone(s) 52 and detection zone(s) 56 of the lateral-flow assay device 20. In one embodiment, the microposts 7 have a height in the interval of about 15 to about 150 μm, preferably about 30 to about 100 μm, a diameter of about 10 to about 160 μm, preferably 40 to about 100 μm, and a gap or gaps between the microposts 7 of about 3 to about 200 μm, preferably 5 to 50 μm or 10 to about 50 μm from each other. The fluid flow path 64 between the sample addition zone 48 and the wicking zone 60 may have a length of about 5 to about 500 mm, preferably about 10 to about 100 mm, and a width of about 0.3 to about 10 mm, preferably about 0.3 to about 3 mm, preferably about 0.5 to 1.5 mm. The microposts 7, according to this device design, are substantially cylindrical in terms of their configuration and cross section. However, their specific design of the microposts 7 can also easily be varied to those of different shapes (e.g., rhombic, hexagonal, etc) and sizes to augment flow, as well as to filter materials, Still referring to FIG. 2, the sample addition zone 48 can receive a fluid sample 101, FIG. 1, from a liquid dispenser, such as a pipette or other suitable device. The sample is typically deposited onto the top of the sample addition zone 48. In various embodiments, a filter material (not shown) is placed within the sample addition zone 48 to filter particulates from the sample or to filter blood cells from blood so that plasma can travel through the lateral-flow assay device 20. In these embodiments, the sample is typically deposited onto the filter material.

The sample then flows, e.g., via capillary action of the microposts, to the reagent zone 52, which can include reagent(s) useful in the reaction, e.g., binding partners such as antibodies or antigens for immunoassays, substrates for enzyme assays, probes for molecular diagnostic assays, or auxiliary materials such as materials that stabilize the integrated reagents, materials that suppress interfering reactions, and the like. Generally, one of the reagents useful in the reaction bears a detectable signal as discussed herein. In some cases, the reagents may react with the analyte directly or through a cascade of reactions to form a detectable signal such as a colored or fluorescent molecule. In one preferred embodiment, the reagent zone 52 includes conjugate material. The term "conjugate" means any moiety bearing both a detection element and a binding partner.

For purposes of this description, a detection element is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored, molecules, molecules producing colors upon reaction, enzymes, radioisotopes, ligands exhibiting specific binding and the like. The detection element also referred to as a label is preferably chosen from chromophores, fluorophores, radioactive labels and enzymes. Suitable labels are available front commercial suppliers, providing a wide range of dyes for the labeling of antibodies, proteins and nucleic acids, There are, for example, fluorophores spanning practically the entire visible and infrared spectrum. Suitable fluorescent or phosphorescent labels include for instance, but are not limited to, fluoroceins, Cy3, Cy5 and the like. Suitable chemiluminescent labels include but are not limited to luminol, cyalume and the like.

Similarly, radioactive labels are commercially available, or detection elements can be synthesized so that they incorporate a radioactive label. Suitable radioactive labels include hut are not limited to radioactive iodine and phosphorus; e.g., $^{125}$I and $^{32}$P.

Suitable enzymatic labels include but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone 56. In a competitive immunoassay, the analyte will interfere with binding of the binding partner in the conjugate to another binding partner, also called a capture element, integrated into the detection zone 56. Example binding partners included in conjugates include antibodies, antigens, analyte or analyte-mimics, protein, etc.

As the sample interacts with the reagent in the reagent zone 52, the detection material begins to dissolve in which a resultant detectable signal is contained within the fluid flow, which is subsequently carried into the adjacent detection zone 56.

Still referring to FIG. 2, the detection zone 56 is where any detectable signal can be read. In a preferred embodiment and attached to the microposts 7 in the detection zone 56 are capture elements. The capture elements can hold binding partners for the conjugate or complexes containing the conjugate, as described above. For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone 56 can include multiple detection zones. The multiple detection zones can be used for assays that include one or more markers. In the event of multiple detection zones, the capture elements can include multiple capture elements, such as first and second capture elements. The conjugate can be pre-deposited on the lateral-flow assay device 20, such as by coating in the reagent zone 52. Similarly, the capture elements can be pre-deposited on the lateral-flow assay device 20 on the detection zone 56. Preferably, both the detection and capture elements are pre-deposited on the lateral-flow assay device 20, or on the reagent zone 52 and the detection zone 56, respectively.

Downstream from the detection zone 56 and along the fluid flow path 64 is the wicking zone 60. The wicking zone 60 is an area of the lateral-flow assay device 20 with the capacity of receiving liquid sample and any other material in the flow path, e.g. unbound reagents, wash fluids, etc. The wicking zone 60 provides a capillary pressure to continue moving the liquid sample through and out the intermediate detection zones 56 of the lateral-flow assay device 20. The wicking zone 60 and other zones of the herein described lateral-flow assay device 20 can include a porous material such as nitrocellulose, or alternatively can be a non-porous structure defined by the microposts 7, as previously described. The wicking zone 60 can further include non-capillary fluid driving means, such as an evaporative heater or a pump. Further details of wicking zones as used in lateral-flow assay devices 20 according to the various embodiments are found in U.S. patent application Ser. No. 8,025,854 and U.S. Patent Application Publication No. 2006/0239859 A1, both of which are incorporated herein by reference in their entireties.

Tests (assays) are typically completed when the last of the conjugate material has moved into the wicking zone 60 of the lateral-flow assay device 20. At this stage, a detection instrument, such as a fluorimeter or similar device, is used to scan the detection zone 56, the detection instrument being, e.g., incorporated within a portable (hand-held or bench top) testing apparatus. The detection instrument that can be used to perform the various methods and techniques described herein can assume a varied number of forms. For example, a mainframe clinical analyzer can be used to retain a plurality of lateral-flow assay devices as described in copending U.S. Patent Application Publication No. 2013/0330713 A1, the entire contents of which are herein incorporated by reference. In a clinical analyzer at least one detection instrument, such as a fluorimeter, can be provided, for example, in relation to an incubator assembly as a monitoring station in which results can be transmitted to a contained processor.

In various examples, the instrument can include a scanning apparatus that is capable of detecting fluorescence or fluorescent signals. Alternatively, an imaging apparatus and image analysis can also be used to determine, for example, the presence and position of at least one fluorescent fluid front of a lateral-flow assay device. According to yet another alternative version, infrared (IR) sensors could also be utilized to track the position of fluid position in the lateral-flow assay device. For instance, an IR sensor could be used to sense the ~1200 nm peak that is typically associated with water in the fluid sample 101 to verify that sample had indeed touched off onto the substrate of the lateral-flow assay device. It should be readily apparent that other suitable approaches and apparatus capable of performing these techniques could be utilized herein.

The microposts 7, FIG. 1, are preferably integrally molded into the substrate 40 from an optical plastic material such as ZEONOR®, such through an injection molding or embossing process. The width of the detection channel 55 in the fluid flow path 64 is typically on the order of about 0.5 mm to about 4 mm, and preferably on the order of about 2 mm. Other portions of the fluid flow path 64 according to various examples can have widths of less than about 0.5 mm, or on the order of about 0.5 mm to about 4 mm, or greater than about 4 mm. Widths of about 1 mm can also be used for detection channel 55, provided sufficient signal for a suitable detection instrument, such as a fluorimeter, can be read even if the reagent plume does not cover the entire width of the detection zone 56.

Components of the lateral-flow assay devices (i.e., a physical structure of the device whether or not a discrete piece from other parts of the device) described herein can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex, Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral-flow assay devices are injection molded from a cyclic olefin polymer (COP), such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

Still referring to FIG. 2, the defined fluid flow path 64 of the lateral-flow assay device 20 or other lateral-flow assay devices described herein can include open or closed paths, grooves, and capillaries. In various embodiments, the fluid flow path 64 comprises a lateral flow path of adjacent ones of the microposts 7, FIG. 1, having a size, shape and mutual spacing such that capillary flow is sustained through the flow path. In one embodiment, the flow path is in a channel within the substrate 40 having a bottom surface and side walls. In this embodiment, the microposts 7 protrude from the bottom surface of the fluid flow path 64. The side walls may or may not contribute to the capillary action of the liquid. If the sidewalls do not contribute to the capillary action of the liquid, then a gap can be provided between the outermost microposts 7 and the sidewalls to keep the liquid contained in the flow path defined by the microposts 7. Preferably, the reagent that is used in the reagent zone 52 and the capture members or detection agent used in the detection zone 56 is bound directly to the exterior surface of the microposts 7 used in the herein described lateral-flow assay device 20.

Figure 3:
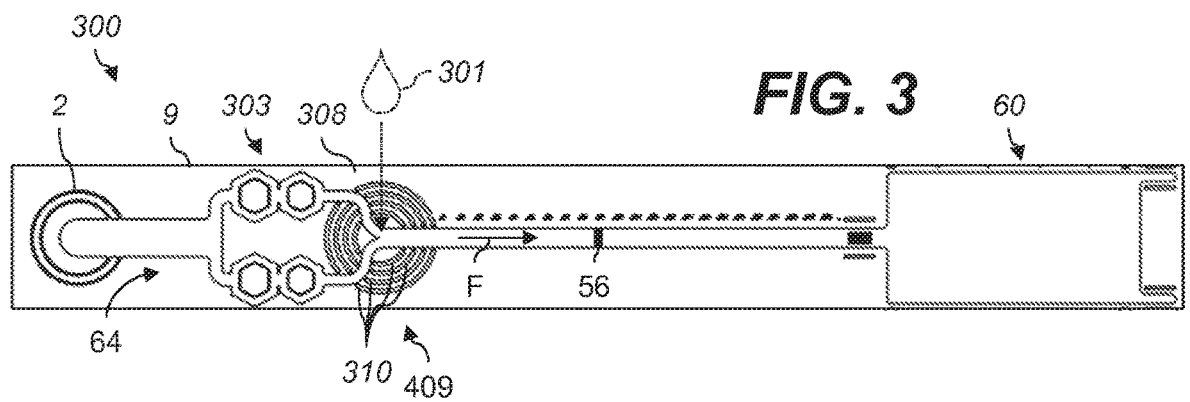
FIG. 3 illustrates a plan view of a lateral-flow assay device made in accordance with at least one embodiment.

FIG. 3 illustrates a plan view of a lateral-flow assay device 300 in accordance with at least one embodiment. The lateral-flow assay device 300 includes the substrate 9 having the sample addition zone 2 and a wash addition zone 409. The sample addition zone 2 and the wash addition zone 409 are disposed along the fluid flow path 64, through which the sample 101, FIG. 1, flows under capillary action in a flow direction F ("downstream") away from the sample addition zone 2 and towards the wash addition zone 409. The fluid flow path 64 is configured to receive a wash fluid 301 (represented in phantom in the wash addition zone 409. For example, the lateral-flow assay device 300 can include a cover having an opening for passage of wash fluid, as discussed below. In another example, the fluid flow path 64 can be an open-channel flow path open to receipt of wash fluid from above.

The lateral-flow assay device 300 includes at least one hydrophilic surface 308 arranged in the wash addition zone 409. The hydrophilic surface 308 is useful with an aqueous wash fluid 301. In an example, the substrate 9 includes, or is coated with or bonded to, a material with which the wash fluid 301 has a contact angle of less than 45°. As used herein, the term "hydrophilic surface" refers specifically to a surface that is wetted by the wash fluid 301. In at least one example, the wash fluid 301 includes numerous surfactants that permit the wash fluid 301 to wet certain types of plastic that are hydrophobic to pure water. Hydrophilic surfaces such as the hydrophilic surface 308 can include such plastics, which are hydrophilic with respect to the wash fluid 301.

The lateral-flow assay device 300 also includes one or more flow constriction(s) 310. As used herein, a "flow constriction" is a structural feature that assists in containing the wash fluid 301 within the wash addition zone 409 or that assists in restricting the wash fluid 310 from spreading out of the wash addition zone 409. Some exemplary flow constrictions narrow the cross-section of flow across the hydrophilic surface 308 or otherwise impede, resist, or arrest (even if only temporarily) the flow of the wash fluid 301 across the hydrophilic surface 308. Examples of flow constrictions include a nozzle nearing the substrate 9, and the substrate 9 turning a corner out of plane, e.g., at the edge of a groove in the substrate 9. Such flow constrictions are discussed below. The flow constriction(s) 310 are spaced apart laterally from the fluid flow path 64, as shown more clearly in FIG. 4.

The flow constriction(s) 310 are arranged to define, with the at least one hydrophilic surface 308, a reservoir 535 (FIG. 5) configured to retain the wash fluid 301 by formation of a meniscus between the hydrophilic surface 308 and the one or more flow constriction(s) 310, as discussed below. The fluid flow path 64 is configured to draw the wash fluid from the reservoir by capillary pressure.

As discussed above with reference to FIGS. 1 and 2, the lateral-flow assay device 300 can include, e.g., in the fluid flow path 64, a plurality of the microposts 7, FIG. 1. The microposts 7 can extend upwardly from the substrate 9 proximal to the wash addition zone 409 or other zones described herein. The microposts 7 have heights, diameters and reciprocal spacing between the microposts 7 that induce lateral capillary flow of the sample 101, the wash fluid 301, or both. Moreover, the lateral-flow assay device 300 can include at least one reagent zone 303, disposed along the fluid flow path 64 downstream of the sample addition zone 2.

Furthermore, the lateral-flow assay device 300 can include at least one detection zone 56 disposed along the fluid flow path downstream of the sample addition zone 2 and the wash addition zone 409. The at least one detection zone 56 can include a detection material responsive to an analyte of the sample 101 to produce a detectable signal, as discussed below with reference to FIG. 37.

Figure 4:
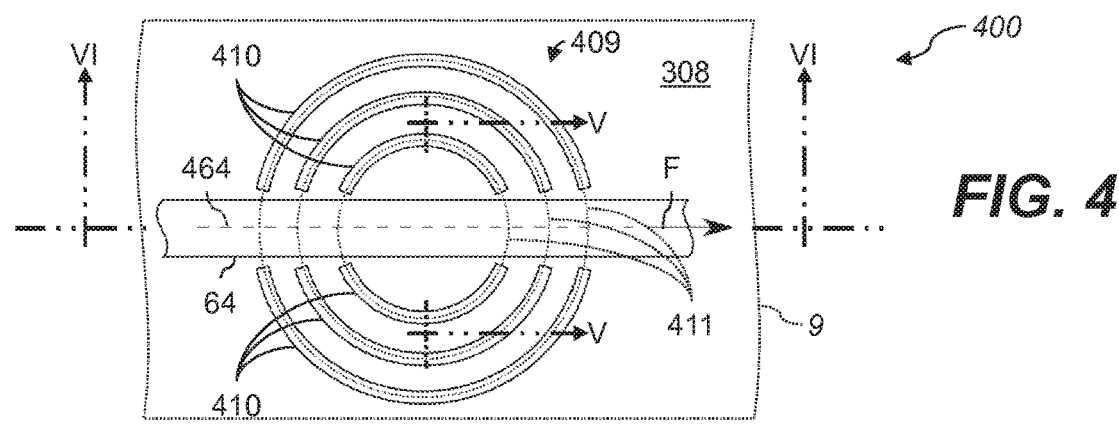
FIG. 4 is a plan view of details of a wash addition zone of a lateral-flow assay device according to an exemplary embodiment.

Referring to FIG. 4, there is shown a plan view of an exemplary lateral-flow assay device 400 according to various embodiments. In aspects such as that shown, groove(s) are used as the only flow constriction(s) 310. For example, the lateral-flow assay device 300 can be an open-top lateral-flow assay device, i.e., a lateral-flow assay device with no cover.

In this example, the substrate 9 includes the at least one hydrophilic surface 308. The one or more flow constriction(s) 310 include at least one groove 410 formed in the hydrophilic surface 308, and laterally within the wash addition zone 409. In various examples, the grooves 410 can be elongated, straight or curved, short, circular or elliptical, or other shapes (when viewed from above). In at least one example, the grooves 410 are elongated and have widths between 50 μm and 200 μm. In other examples, the widths of the grooves 410 can be between 5 μm and 1000 μm, or can be greater than 1000 μm.

In the example shown, the lateral-flow assay device 400 includes a plurality of the flow constriction(s) 310, each of the flow constrictions 310 including groove(s) 410 formed in the hydrophilic. surface 308. The groove(s) 410 are arranged along respective arcuate paths 411 about the centerline 464 of the fluid flow path 64. The respective arcuate paths 411 can be circular, elliptical, or another shape. Circular grooves advantageously provide greater stability, since capillary pressure operates to pull the wash fluid 301 into a circular configuration in the absence of flow constriction(s) 310. Accordingly, in at least one example, the grooves 410 are circularly arcuate in shape to maintain a round fluid dome above the fluid flow path 64. The geometric center of the arcuate path for each of the grooves 410 is preferably on the geometric centerline of the fluid flow path 64 if the fluid flow path 64 is straight, as in this example, so that the wash fluid 301 enters the fluid flow path 64 symmetrically along the centerline of the fluid flow path 64.

As noted above with reference to FIG. 3, the grooves 410 are spaced apart laterally from the fluid flow path 64. This spacing advantageously restricts or impedes the wash fluid 301 or the sample 101 in the fluid flow path 64 from flowing into the grooves 410 by capillary pressure.

In various examples, such as that shown, the flow constriction(s) 310, FIG. 3, include at least three spaced-apart grooves 410, e.g., four spaced-apart grooves, formed in the hydrophilic surface 308. In various examples, such as that shown, at least one of the grooves 410 is arranged along a substantially arcuate path 411 disposed substantially about a portion of the fluid flow path 64. Aspects using a plurality of grooves advantageously are more robust to different wash fluid volumes (e.g., permitting a reduction in the precision with which volumes of the wash fluid 301 should be metered) or provide increased reliability of maintaining the dome shape of the reservoir 535, FIG. 5, in case the inner groove is covered by the wash fluid 301 during dispensing, or due to imperfections in the grooves 410 that permit the spread of the wash fluid 301 over the substrate 9.

Figure 5:
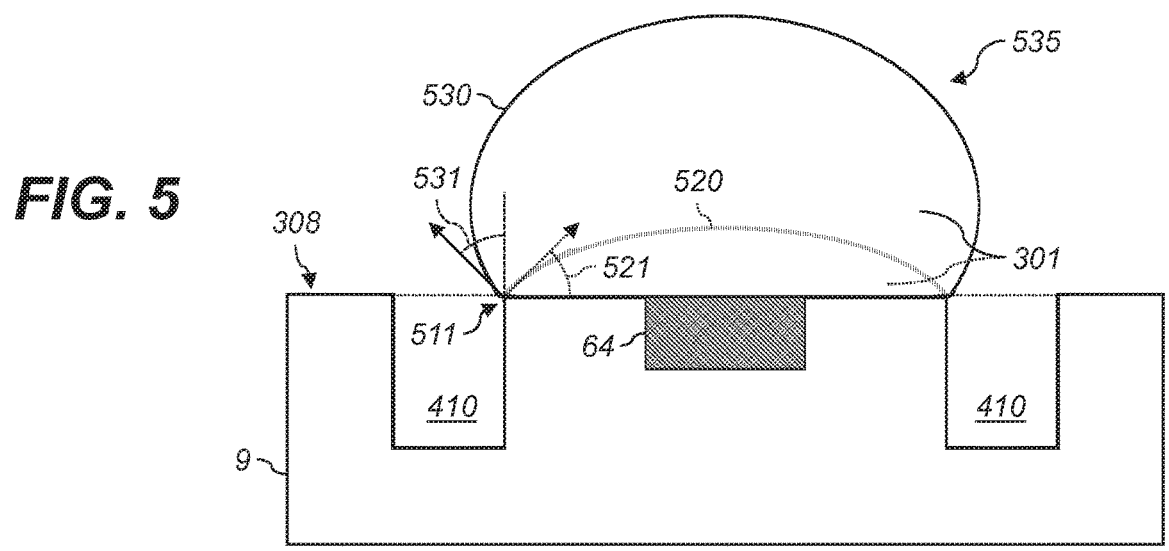
FIG. 5 is a front elevational section along the line V-V in FIG. 4 and shows flow tionsconstric according to an exemplary embodiment.

FIG. 5 is a front elevational section along, the line V-V in FIG. 4 and shows flow constrictions according to various aspects. The substrate 9 has the fluid flow path 64 recessed therein. Two of the flow constrictions 310, FIG. 3, are the grooves 410 recessed into the substrate 9 within the area covered by the hydrophilic surface 308. The illustrated grooves 410 have substantially rectangular cross-sections. The wash fluid 301 wets the hydrophilic surface 308 to form a dome-shaped meniscus 520, 530 above the fluid flow path 64 due to capillary pressure and surface tension. The volume of a reservoir 535 bounded by the meniscus 520, 530 is variable, depending on the volume of the wash fluid 301 delivered by a wash-metering mechanism 3725, FIG. 37. The sizes of the meniscus 520,, 530 and the reservoir 535 shrink as the wash fluid 301 is drawn from the reservoir 535 into the fluid flow path 64 to perform the wash.

The reservoir 535 provides a stable meniscus that advantageously accommodates a wide range of volumes of the delivered wash fluid (e.g., between 7 and 17 μL) while keeping substantially the same wash performance. Another advantage of a fluid meniscus 520, 530 is that it can buffer large variations in the delivery rate of the wash fluid 301. The grooves 410 in the illustrated embodiment also advantageously assist in maintaining a round shape of the wash fluid 301 in the reservoir 535 at the hydrophilic surface 308.

In a hypothetical example using a wash fluid 301 with a contact angle of 45° against the hydrophilic surface 308, if the hydrophilic surface 308 were flat and did not have the grooves 410 (graphically represented by the dotted lines across the tops of the grooves 410), a meniscus 520 (shown stippled) would form. The contact angle of 45° in this hypothetical example is shown at an angle 521 with respect to the horizontal hydrophilic surface 308.

In an example using the wash fluid 301 with the contact angle of 45° and with the grooves 410, a meniscus 530 forms. The 45° contact angle is shown at an angle 531 with respect to the vertical edge of the grooves 410. The volume under the meniscus 530 is the reservoir 535 defined by the groove(s) 410, i.e., the flow constriction(s), and the at least one hydrophilic surface 308. The reservoir 535 is configured to retain the wash fluid 301 by formation of the meniscus 530 between the hydrophilic surface 308 and the one or more flow constriction(s) 310.

The wash fluid 301 is drawn around the corner 511 by surface tension and contact forces, and consequently the cross-sectional area of the flow is restricted. The grooves 410 and the resultant angle 531 raise the meniscus 530 compared to the meniscus 520. This increases the radius of the reservoir 535, increasing or substantially increasing the volume of the reservoir 535. For example, hemispherical reservoirs have the volumes indicated in Table 1, below, for various radii. As can be seen, increasing radius rapidly increases volume.

TABLE 1

|  | R (mm) | | | | |
| --- | --- | --- | --- | --- | --- |
|  | 1 | 1.25 | 1.5 | 1.75 | 2 |
| V (µL) | 2.1 | 4.1 | 7.1 | 11.2 | 16.7 |

Accordingly, using the grooves 410 or similar flow constrictions 310 surrounding the fluid flow path 64 can advantageously permit maintaining and controlling the shape of the meniscus 530 and of the reservoir 535 to increase the volume of the reservoir 535 above the fluid flow path 64.

Figure 6:
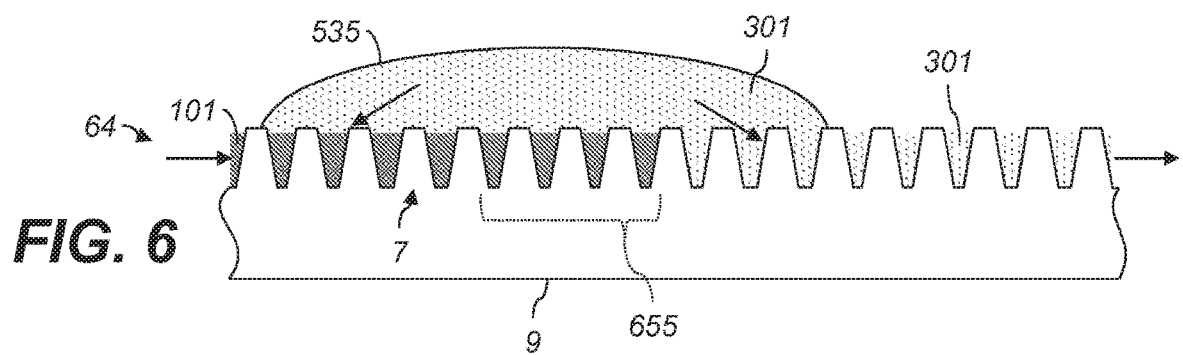
FIG. 6 is a side elevational section along the line VI-VI in FIG. 4 and shows wash fluid ingress into a fluid flow path according to an exemplary embodiment.

FIG. 6 is a side elevational section along the line VI-VI in FIG. 4, and shows ingress of the wash fluid 301 into the fluid flow path 64. The reservoir 535 is shown arranged over the fluid flow path 64, and holding the wash fluid 301. In this example, the fluid flow path 64 includes the microposts 7 arranged over the substrate 9. The sample 101 has filled at least a portion of the fluid flow path 64. In various examples, the wash fluid 301 enters fluid flow path 64 from the reservoir 535 proximate the edge of the reservoir 535, e.g., being drawn by capillary pressure between the microposts 7.

In various exemplary configurations using the microposts 7, the wash fluid 301 is dispensed into the fluid flow path 64 between the sample addition zone 2 and the detection zone 56 to interrupt or displace the fluid of the sample 101. The wash fluid 301 forms a dome shaped meniscus above the fluid flow path 64 so that fresh wash fluid 301 enters the fluid flow path 64 from above the fluid flow path 64 while the flow of sample stops flowing toward the reaction zone. A dome shaped wash fluid meniscus above the fluid flow path 64 is advantageous since the flow resistance is the smallest from above the fluid flow path 64 as compared with sample fluid flowing through between the microposts 7. This low flow resistance will stop sample flow while supplying fresh wash fluid 301 from the front edge of the reservoir 535. Prior geometry designs using a shallow well in a wash addition area do not reliably maintain the dome shape of the dispensed wash fluid 301. The wash fluid 301 can easily spread and result in a thin layer of the wash fluid 301 above the fluid flow path 64 instead of a dome, especially when the wash fluid 301 has a low contact angle for the hydrophilic surface 308, FIG. 3 (e.g. if the contact angle is 45°). In this case, wash efficiency is poor since little of the wash fluid 301 above the fluid flow path 64 is available and sample 101 will continue to flow even after the addition of wash fluid. Configurations described herein advantageously maintain the reservoir 535 to effectively supply the wash fluid 301 to the fluid flow path 64.

Specifically, in at least one example, the wash fluid 301 has a large amount or a relatively high concentration of surfactants. These surfactants are useful for washing, but increase the difficulty of drawing from a thin layer of the wash fluid 301 into the fluid flow path 64. Accordingly, in this example it is preferable to maintain a bulk fluid in the reservoir 535 from which the fluid flow path 64 can draw. The grooves 410, FIG. 5, advantageously increase the size of the reservoir 535, permitting more effective flow of the wash fluid 301 into the fluid flow path 64 than in prior schemes with no flow constrictions.

In the example of FIG. 5, the sample 101 has filled the fluid flow path 64, the wash fluid 301 has been applied, and the wash fluid 301 has begun to displace the sample 101 in the fluid flow path 64. The wash fluid 301 can flow both downstream (along the flow direction F) and upstream (opposite the flow direction F). In various aspects, the wash fluid flows faster downstream than upstream. In an example, there is an area 655 of the fluid flow path 64 at least partly under the reservoir 535 in which there is no flow, i.e., in which the contents of the fluid flow path 64 are stagnant.

Figure 7:
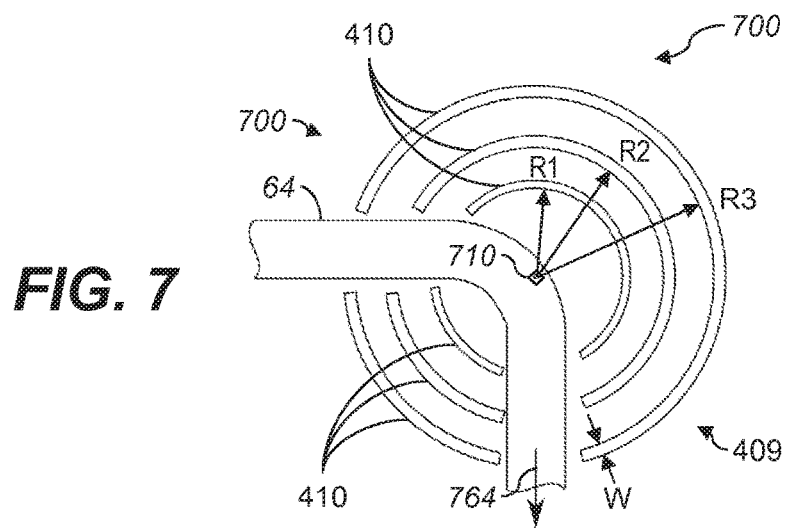
FIGS. 7 and 8 are plan views of exemplary groove configurations in wash addition areas according to various embodiments.

Referring to FIG. 7, there is shown a plan view of an exemplary groove configuration of a lateral-flow assay device 700 according to various embodiments. The fluid flow path 64 in the exemplary lateral-flow assay device 700 has a 90° bend in the wash addition zone 409. In this example, at least one of the grooves 410 is disposed substantially about a reference point 710 along a centerline 764 of the fluid flow path 64 leaving the wash addition zone 409. This placement of the reference point 710, i.e., the geometry center of the grooves 410, advantageously maintains symmetry in the flow of the wash fluid 301 along the fluid flow path 64 departing the wash addition zone 409.

Also as shown here, it is not required that each of the grooves 410 or other flow constriction(s) 310, FIG. 3, have the same width W or other dimensions. In this example, the grooves 410 are arranged along substantially arcuate paths (not shown) having respective radii, e.g., radii R1, R2, R3, with respect to the reference point 710.

Figure 8:
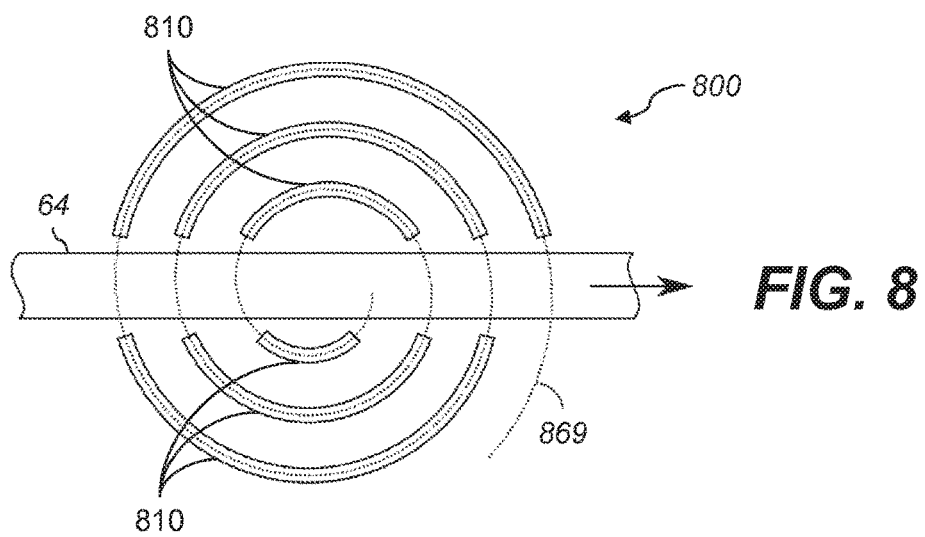

Referring to FIG. 8, there is shown a plan view of an exemplary groove configuration of a lateral-flow assay device 800 according to various embodiments. In this example, at least one of the groove(s) 410 is configured as a segment of a spiral. The segment can have any length and number of turns (for the avoidance of doubt, fractional turns and grooves 410 with less than one full turn can be used). As a result, one or more of the groove(s) 410 can be a spiral passing through more than 360° of rotation around a center point. However, this is not required.

In the example shown, the grooves 810 are arranged along a spiral path 869. The spiral path 869 is arranged to laterally extend on either side of the fluid flow path 64. Accordingly, each of the grooves 810 follows the spiral path 869 until blocked by the fluid flow path 64. In this and other aspects, the fluid flow path 64 and the grooves 410 (or, in various aspects, others of the flow constrictions 310) are separated by a barrier or gap so that fluid in the fluid flow path 64 is restricted from flowing to the grooves 410 by capillary pressure.

Various aspects using grooves 410 around the fluid flow path 64 maintain and control the meniscus shape of the wash fluid 301 so that a higher dome will be formed above the fluid flow path 64 and the wash fluid 301 will be restricted from spreading beyond the grooves 410.

Figure 9:
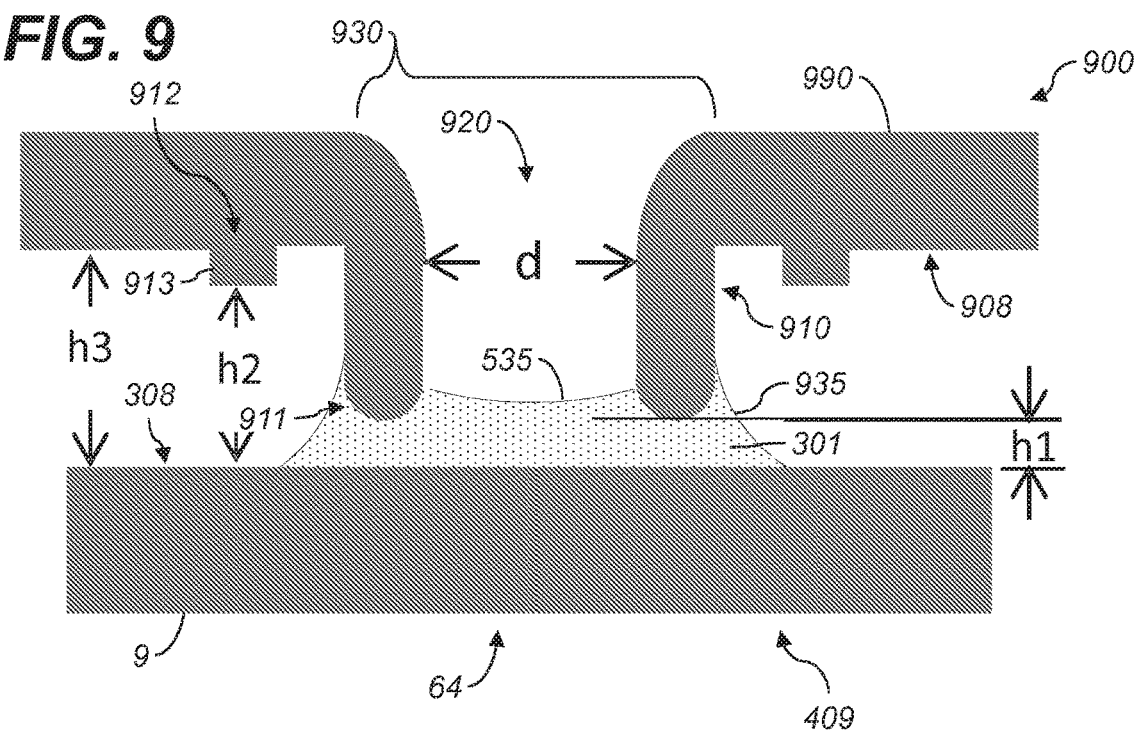
FIGS. 9 and 10 are elevational sections of an exemplary lateral-flow assay device according to various embodiments and illustrate stages in which fluid fills an internal volume of the assay device.
Figure 10:
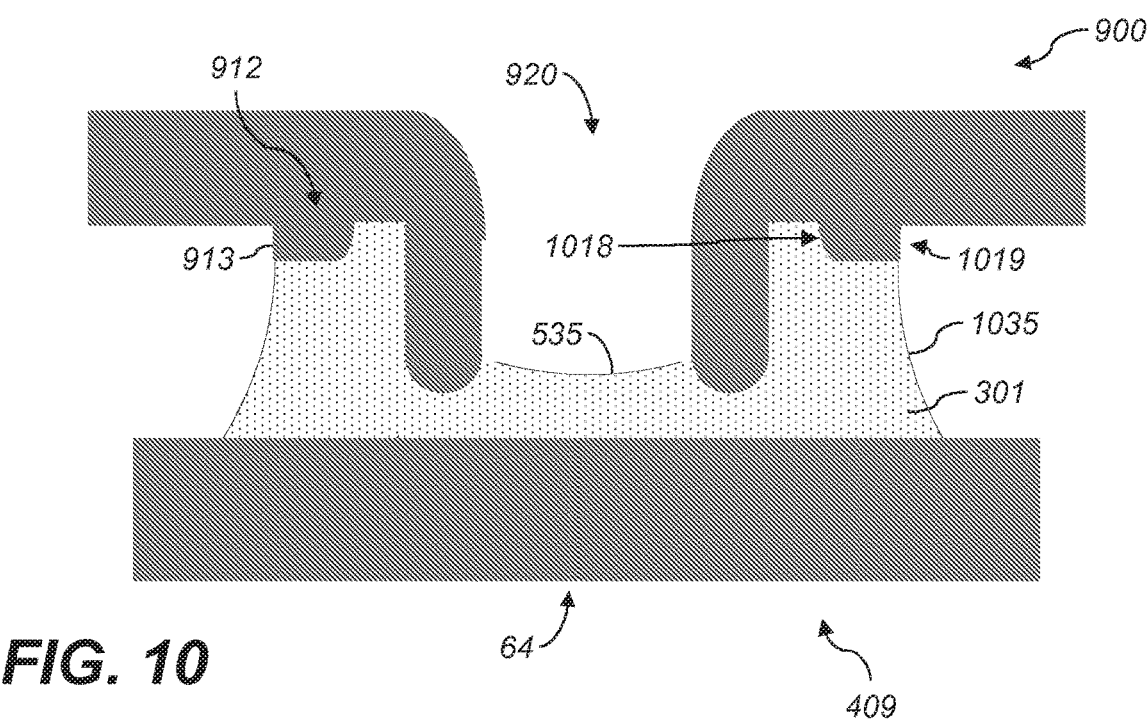

Referring to FIGS. 9 and 10, there are shown elevational sections of an exemplary lateral-flow assay device 900 in accordance with at least one embodiment. FIGS. 9 and 10 illustrate stages in which fluid fills an internal volume of the lateral-flow assay device 900. The exemplary lateral-flow assay device 900 does not use grooves 410, FIG. 8, as its flow constriction(s) 310, FIG. 3. Instead, the lateral-flow assay device 900 includes a cover 990 arranged over the substrate 9. The cover 990 includes the hydrophilic surface 908 facing the substrate 9. The substrate can also have a hydrophilic surface 308, but this is not required. The cover 990 also includes an aperture 920 of diameter d defining a wash port 930 at least partly aligned with the wash addition zone 409. The aperture 920 is configured to receive the wash fluid 301.

At least one of the flow constriction(s) 310 comprises a first cover flow constriction 910, including a protrusion 911 (e.g., a nozzle or nub; examples are discussed below) extending from the cover 990 towards the substrate 9 proximate the aperture 920. In the example shown, the first cover flow constriction 910, and specifically the protrusion 911, includes a lip of the aperture 920 protruding to a first predetermined distance h1 from the substrate 9. Also in the example shown, a second cover flow constriction 912 is arranged outside the aperture 920 and includes a protrusion 913 extending to a second predetermined distance h2 from the substrate 9. The second predetermined distance h2 can be greater than the first predetermined distance h1, as shown. In other configurations, h2>h1, h2≈h1, or h2=h1. As used herein, "higher" or "deeper" cover protrusions are those that extend relatively farther from the cover; "shorter" or "shallower" cover protrusions are those that extend relatively less far from the cover 990.

The example of FIGS. 9 and 10 can represent a nozzle (the cover flow constriction 910 with the interior aperture 920) having an inside diameter d. The nozzle can convey the wash fluid 301 from a fluid supply (not shown; e.g., a pipette or blister) to the hydrophilic surface 908 or to the hydrophilic surface 308 (if present). The nozzle can be annular in plan, e.g., ring structure. The second cover flow constriction 912 can be an outer ring. Outside the double outer ring structure (cover flow constrictions 910, 912), the gap distance between the hydrophilic surface 908 and the facing surface of the substrate 9 is h3, which is larger than h2 in this example. The inner ring (the protrusion 911) advantageously retains the wash fluid 301 in the reservoir 535 when the delivered fluid volume is small, e.g., 5 to 7 µL. The outer ring (the protrusion 913) is spaced farther from the surface of the substrate 9 (h2>h1) so that more fluid, e.g., 15 to 17 µL, can be retained within a limited spatial extent (e.g., a diameter of the wash addition zone 409 substantially equal to 5 mm).

Referring specifically, FIG. 9, in an example, d=2 mm, h1=0.35 mm, h2=0.8 mm, and h3=1 mm. The outside diameter of the protrusion 911 is 3 mm. The inner diameter of the protrusion 911 is 4 mm, and the outer diameter of the protrusion 913 is 5 mm. Under the protrusion 911, the volume of the gap is about 2.5 µL. The gap volume between the protrusions 911, 913 is 5.5 µL. The gap volume under the protrusion 913 is 4.6 µL. The total volume under the three parts is 12.6 µL. Since meniscus shape is not exactly straight, experiments showed that the feature can maintain stability and provide normal wash for a wash volume of 5 to 20 µL.

FIG. 9 shows the reservoir 535 when a relatively smaller amount of the wash fluid 301 has been added compared to FIG. 10. In this example, the hydrophilic surface 308 is used. The rounded end of the protrusion 911 permits the wash fluid 301 to form a dome in the nozzle (the aperture 920) and more readily contact the hydrophilic surface 308. Specifically, the rounded end reduces back pressure to permit easier dispensing into the wash addition area 409 through the aperture 920. A round bottom reduces back pressure by providing an increased radius as the meniscus of the wash fluid 301 moves down the aperture 920 towards the substrate 9. This permits the wash fluid 301 to contact the substrate 9 or the hydrophilic surface 308 thereof without a large allied pressure. This can be particularly useful, e.g., with uncoated plastic nozzles with which the wash fluid 301 has a contact angle of, e.g., 100°.

Upon contact, the wash fluid 301 wets the hydrophilic surface 308 and thus spreads laterally. The lateral spreading causes the wash fluid 301 to also wet the hydrophilic surface 908. Capillary pressure forms menisci, e.g., a meniscus 935, that define the reservoir 535 as shown.

Referring specifically to FIG. 10, there is shown the reservoir 535 when a relatively larger amount of the wash fluid 301 has been added compared to FIG. 9, e.g., 15 µL. In this example, the meniscus 1035 is stabilized by the protrusion 913 (the outer ring). The reservoir 535 is defined by the meniscus 1035 and a meniscus (shown) inside the aperture 920.

Also in the example of FIG. 10, a first one of the flow constriction(s), e.g., the cover flow constriction 912 including the protrusion 913, includes a proximal edge 1018 and a distal edge 1019 defined with respect to the fluid flow path 64. The distal edge 1019 is more sharply curved than the proximal edge 1018. This advantageously increases the dome height at the distal edge 1019, e.g., as discussed above with reference to the angle 531, FIG. 5. In other aspects, the proximal edge 1018 is more sharply curved than the distal edge 1019, or the edges 1018, 1019 are equally sharply curved. The curvature of the edges 1018, 1019 can be selected to determine the volume that can be held the reservoir 535 when the menisci 1035 are retained at the respective one of the edges 1018, 1019. Increasing the sharpness of curvature of the edges 1018, 1019 increases the effectiveness with which the edges 1018, 1019 "pin" (retain) menisci.

Figure 11A:
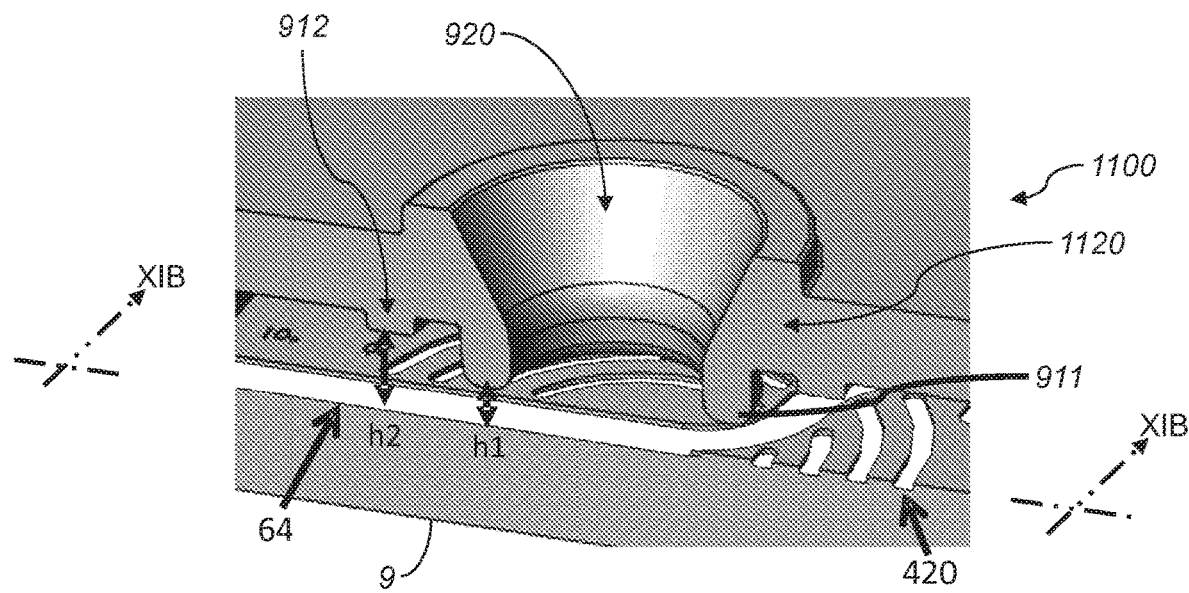
FIG. 11A is a sectioned perspective of a lateral-flow assay device according to various aspects.
Figure 11B:
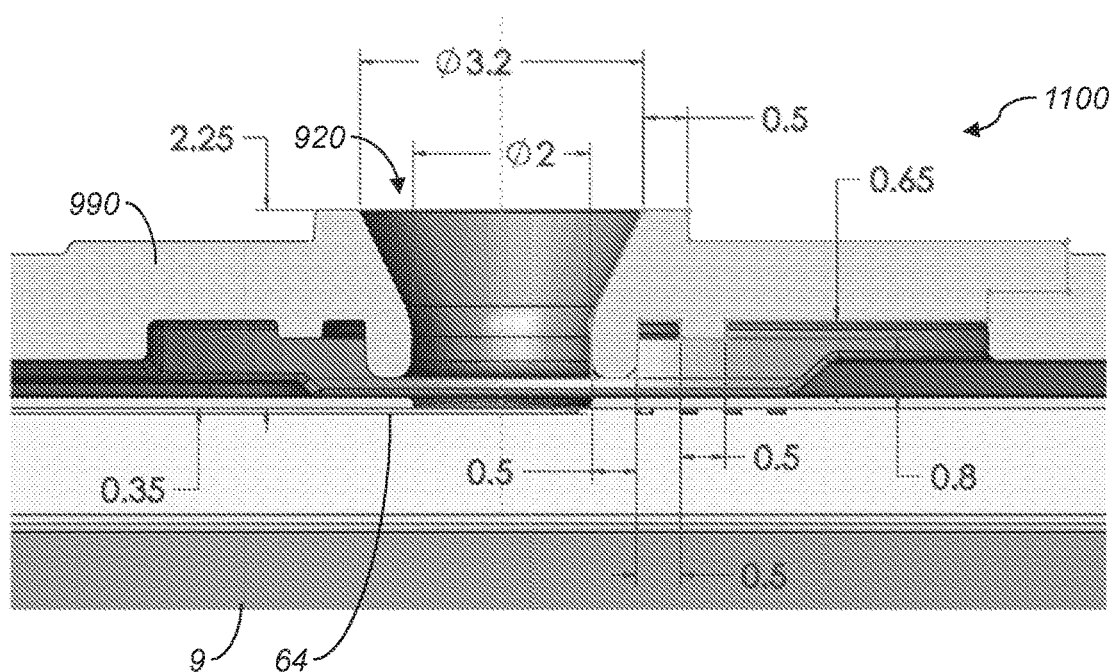
FIG. 11B is an elevational section along the line XIB-XIB in FIG. 11A.

FIG. 11A is a sectioned perspective of a lateral-flow assay device 1100 according to various aspects, and. FIG. 11B is an elevational section along the line XIB-XIB in FIG. 9A. In the section shown in FIG. 11B, dimensions are given in millimeters. As shown, the lip of the aperture 920 is substantially annular in shape. Since capillary force naturally tries to maintain circular configurations, using an annular nozzle can advantageously improves stability of menisci such as that shown in FIG. 9. Also as shown, in this example, the aperture 920 and the lip of the aperture (the protrusion 911) are coaxial to one another.

In this example, the cover 990 of the lateral-flow assay device 1100 is arranged over the substrate 9. At least one of the flow constriction(s) 310 includes the nozzle 1120 extending from the cover 990 towards the substrate 9 and spaced apart from the substrate 9. The nozzle defines a wash port 930, FIG. 9, at least partly aligned with the wash addition zone 409, FIG. 9, and configured to receive the wash fluid 301, FIG. 9. At least one said flow constriction 310 can include an annulus (the cover flow constriction 912) arranged around the nozzle 1120 and extending a. smaller distance from the cover 990 than does the nozzle 1120. The aperture 920 in the nozzle 1120 can be conical, as shown. This can provide humans dispensing the wash fluid 301 through the nozzle 1120 a larger target to hit, reducing the probability of spilling the wash fluid 301. This can also assist in drawing the wash fluid 301 towards the substrate 9, since the reduction in diameter of the aperture 920 causes the capillary pressure pulling the wash fluid 301 down near the bottom of the aperture 920 to exceed the capillary pressure pulling the wash fluid 301 up near the wider top of the aperture 920. Alternatively, the nozzle 1120 can have a cylindrical or rectilinear aperture 920, or an aperture 920 of another shape.

In various aspects such as that shown in FIGS. 11A and 11B, nozzle(s) 1120 and groove(s) 420 are used together. The nozzles(s) 1120 and the groove(s) 420 both assist in maintaining meniscus stability and restricting the metered wash fluid 301 from spreading across the hydrophilic surface 308 of the substrate 9. Various such aspects are discussed below with reference to FIGS. 12, 13, and 15-19. Moreover, various exemplary configurations of flow constrictions are described below. Unless otherwise specified, flow constrictions shown on substrates or on covers can be used independently or can be used together in any combination.

Referring to FIG. 12, there is shown an elevational section of an exemplary lateral-flow assay device 1200 and an illustration of effects of contact angle. In this example, the lateral-flow assay device 1200 includes the substrate 9 having the hydrophilic surface 308 facing the cover 990. The one or more flow constriction(s) 310 include one or more recessed substrate flow constriction(s), in this example the grooves 1210. For example, groove(s) 1210 and nozzle(s) 1120 can be used together when the contact angle of the wash fluid 301 on the hydrophilic surface 308 is less than 40°. At least one of the substrate flow constriction(s) can be arranged along a substantially arcuate path 411, FIG. 4, disposed substantially about a portion of the fluid flow path 64, e.g., as shown in FIG. 11A.

As the wash fluid 301 is added to the lateral-flow assay device 1200 through the aperture 920, it wets the hydrophilic surface 908 of the cover 990 and the facing hydrophilic surface 308 of the substrate 9 and forms menisci. In an example, the wash fluid 301 creeps along the hydrophilic surface 908 on the underside of the cover 990. The shape of the meniscus and thus the lateral extent of the reservoir 535 for a given volume of the wash fluid 301 can be controlled by selecting materials having desired contact angles. In an example in which the wash fluid 301 has a contact angle of less than 45° with the hydrophilic surfaces 308, 908, one or more menisci 1235 form. In an example in which the wash fluid 301 has a contact angle of greater than 45° with the hydrophilic surfaces 308, 908, one or more menisci 1237 form. As shown, the menisci 1237 extend farther from the aperture 920 than do the menisci 1235. Accordingly, in various aspects, the compositions of the wash fluid 301 and the hydrophilic surfaces 308, 908 are selected to provide a desired lateral extent of the reservoir 535.

Moreover, the sizes and positions of the substrate flow constriction(s), e.g., the groove(s) 1210, can be selected to cooperate with the nozzle 1120, in this example, four grooves 1210, 1211, 1212, 1213 are visible (referred to collectively with reference number 1210). The grooves 1210 are configured so that the grooves 1210 farther from the aperture 920 will participate in forming reservoirs with larger volumes than the grooves 1210 closer to the aperture. For example, the groove 1213 can retain a meniscus behind which more of the wash fluid 301 is held than can the groove 1211. In this non-limiting example, meniscus 1235 is held by the proximal edge (for clarity, not labeled) of the groove 1212, and the meniscus 1237 is held by the distal edge of the groove 1213.

In various aspects, the wash fluid 301 can form a stabilized meniscus at a location at which the gap size, i.e., the distance between the hydrophilic surfaces 308, 908, is smaller at that location than at adjacent locations. The grooves 1210 cause this to be the case for the raised areas between the grooves, and the cover flow constrictions cause this to be true between the cover flow constrictions and the hydrophilic surface 308.

FIG. 13 is an elevational section of an exemplary lateral-flow assay device 1300 illustrating stages in which the wash fluid 301 fills an internal volume of the lateral-flow assay device 1300. For clarity, the stages are indicated with circled numbers, and menisci are indicated with dotted curves. Each of stages 2, 3, and 4 includes the wash fluid 301 in the areas marked indicated by earlier stages, starting from stage 2.

In stage 1, the wash fluid 301. is retained within the nozzle 1120 and forms a dome, as described above In stage 2, the wash fluid 301 is retained between the protrusion 911 (the lip of the nozzle 1120) and the hydrophilic surface 308. The menisci are concave. In an example, the reservoir 535 holds about 5 µL in stage 2.

In stage 3, more of the wash fluid 301 has been added. The volume of the reservoir 535 has expanded, so the menisci between the hydrophilic surface 308 and the protrusion 311 are convex rather than concave. As a result, the reservoir 535 holds, e.g., about 7 µmL in stage 3.

In stage 4, more of the wash fluid 301 has been added, and the reservoir 535 has expanded to the menisci 1335. In an example, the reservoir 535 holds about 20 µmL in stage 4.

FIG. 13 shows one example of a configuration of flow constrictions 310, FIG. 3, that provides a reservoir 535 with a selected capacity in each of a selected number of steps. The number and arrangement of the flow constrictions 310, e.g., the nozzle 1120 or other cover flow constrictions, or the grooves 1210 or other substrate flow constrictions, can be selected to effectively retain the wash fluid 301 in the reservoir 535 above the fluid flow path 64. For example, the flow constrictions 310 can be configured to effectively retain volumes of the wash fluid 301 in 2 µL increments. Each set of flow constrictions, e.g., each ring protruding from the hydrophilic surface 908, provides a range of stable volumes of the reservoir 535. In this example, the protrusion 911 provides stable ones of the reservoirs 535 between volumes of 5 µmL (stage 2) and 7 µL (stage 3). These ranges, and configurations using multiple flow constrictions, increase the range of possible uses of a single design of the lateral-flow assay device 1300.

Figure 14:
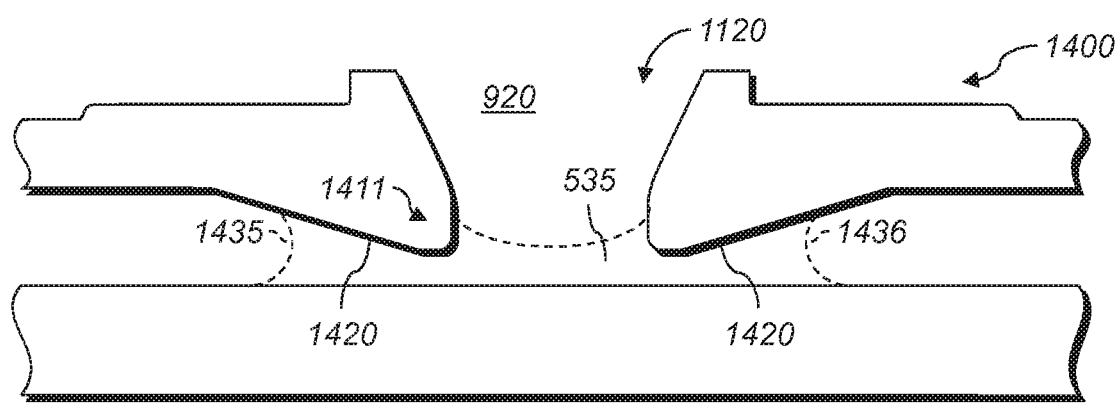
FIG. 14 is an elevational section of another exemplary lateral-flow assay device.

FIG. 14 is an elevational section of another exemplary lateral-flow assay device 1400. The lateral-flow assay device 1400 includes the nozzle 1120 having a lip 1411 (a cover flow constriction 910, FIG. 9). The lip 1411 has a distal surface 1420 with respect to the aperture 920. The distal surface 1420 is sloped and does not have a sharply-curved edge. Capillary pressure will tend to retain the wash fluid 301, FIG. 13, in the reservoir 535 as long as the menisci 1435, 1436 contact the sloped distal surface 1420. Since capillary pressure is stronger in narrower apertures, if the reservoir 535 moves, e.g., right, the capillary pressure, pulling the meniscus 1435 to the left will increase and the capillary pressure pulling the meniscus 1436 to the right will decrease, returning the reservoir 535 to a more central position.

FIGS. 15-27 are perspectives of components of lateral-flow assay devices according to various aspects. FIGS. 15-18 show examples similar to those discussed above with reference to FIGS. 11A-11B. FIG. 15 shows a configuration with a single ring (the lip of the nozzle) spaced apart from the surface of the substrate 9 by 0.75 mm. FIG. 16 shows a configuration similar to that of FIG. 15, but with the ring spaced apart from the substrate by 0.35 mm. This configuration can be useful, e.g., for lateral-flow assay devices designed for only a single volume of the wash fluid 301. FIG. 17 shows a configuration having two rings, each spaced apart by 0.35 mm. FIG. 18 shows a configuration having two rings, the inner (the lip of the nozzle) spaced apart by 0.75 mm and the outer spaced apart by 0.35 mm. Exemplary devices were constructed according to configurations shown in FIGS. 15-18 and were tested. The results are given in Table 2, below.

Table 2 shows the wash performance of the four wash feature designs shown in FIGS. 15-18 at different wash volumes. The wash fluid used in this test was POC wash having properties listed below in Table 3. In Table 2, "overflow" signifies that wash fluid flowed above the fluid flow path 64 (this is undesirable since the wash efficiency will be poor). "Meniscus out" signifies that the fluid meniscus extends laterally at least partly beyond the third wash groove 410, FIG. 4, in the tested lateral-flow assay device. "Off-center" signifies that the fluid meniscus is not centered in the tested arcuate grooves 410. "Good" signifies that the wash fluid 301 is stable in the reservoir 535, FIG. 5, and the meniscus is substantially a desired size. Cells in Table 2 marked "*" represent preferred embodiments.

TABLE 2 experimental results

| | Gaps | | Metering volume and fluid types | | | | |
|---|---|---|---|---|---|---|---|
| FIG. | Inner ring | Outer ring | *5 µL POC | *10 µL POC | *15 µL POC | 20 µL POC | 25 µL POC |
| 15 | 0.75 | N/A | over-flow | *good | good | stable, brief over-flow | stable, brief overflow, meniscus out |
| 16 | 0.35 | N/A | *stable, fluid short | *good | *good | stable, long over-flow | stable, long overflow, meniscus out |
| 17 | 0.35 | 0.35 | *stable, fluid short | *good | *good | stable, brief over-flow | stable, long overflow, meniscus out |
| 18 | 0.75 | 0.35 | stable, off-center, brief overflow | *stable, brief over-flow | *stable, brief over-flow | *stable, brief over-flow | stable, brief overflow, meniscus out |

FIG. 17 illustrates a configuration in which at least one of the flow constriction(s) 310 includes an annulus 1710 arranged around the nozzle 1120 and extending substantially the same distance from the cover 990 as does the nozzle 1120.

In an example (not shown), the annulus 1710 can be interrupted periodically, e.g., every 90° around the annulus 1710, thus forming a plurality of independent arcuate protrusions.

FIG. 18 illustrates a configuration in which at least one of the flow constriction(s) 310 includes an annulus 1810 arranged around the nozzle 1120 and extending a larger distance from the cover 990 than does the nozzle 1120.

Figure 19:
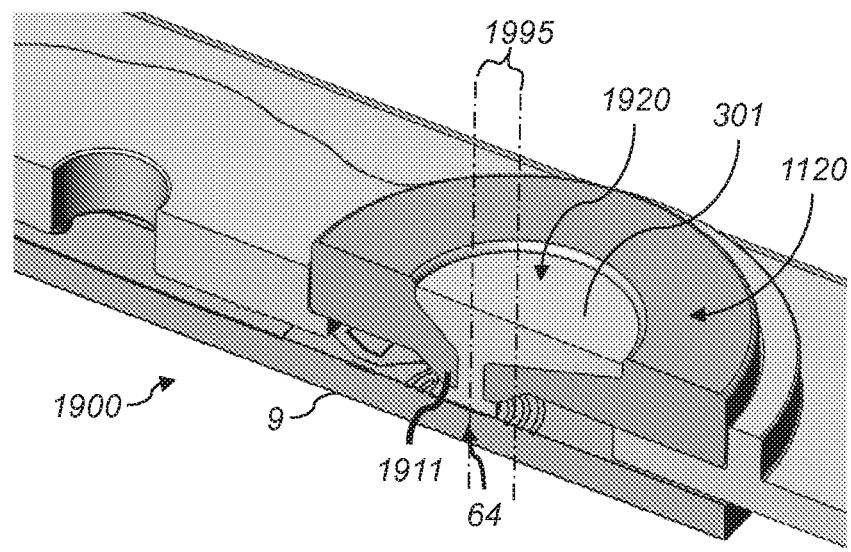

FIG. 19 is a top perspective view of components of a lateral-flow assay device according to various aspects. In the illustrated configuration, the aperture 1920 of the nozzle 1120 and the lip 1911 of the aperture 1920 are axially offset from one another. The wash fluid 301 is shown filling the aperture 1920 and being dispensed onto the substrate 9. For clarity of explanation, the axes of the lip 1911 and of the aperture 1920 are shown, as is the offset 1995 between them in this example. Axial offset provides increased flexibility in the design of the lateral-flow assay device 1900, since the location at which the wash fluid 301 is received (the aperture 1920) can be offset from the location at which the wash fluid 301 is dispensed onto the substrate 9. In an aspect, the lowest tip of the aperture 920 is disposed above the fluid flow path 64 to be washed. Also as shown, the aperture 1920 can have a partly-conical, partly-cylindrical shape.

Figure 20:
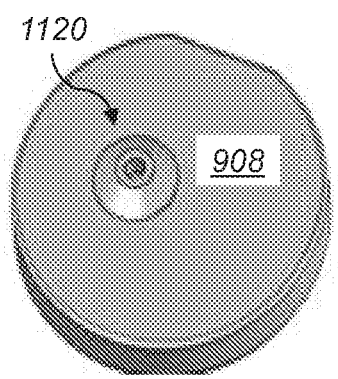

FIG. 20 is a perspective of components of the lateral-flow assay device 1900, FIG. 19, according to various aspects. FIG. 20 shows a bottom perspective view of the nozzle 1120. As shown, the nozzle 1120 has a conical portion, as indicated. FIG. 20 also shows a portion of the hydrophilic surface 908. Accordingly, in various embodiments, a first one of the flow constriction(s) 310 is shaped substantially as a convex closed figure such as a cone. Convex closed figures can include nubs, e.g., circular, elliptical, or polygonal in planwise cross-section.

Figure 21:
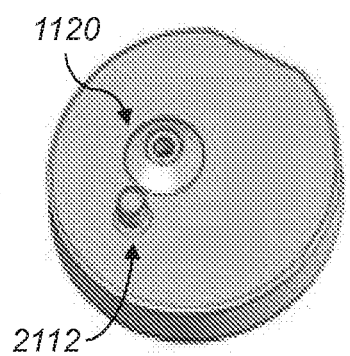

FIG. 21 is a bottom perspective view of components of a lateral-flow assay device according to various aspects. In the illustrated configuration, at least one of the flow constrictions 310 includes a protrusion 2112 spaced apart from the nozzle 1120. The protrusion 2112 permits menisci to form to differentially attract to a known location any excess wash fluid beyond the amount that can be held in a reservoir 535, FIG. 5, formed by the nozzle 1120 alone. This can advantageously permit, e.g., drawing excess amounts of the wash fluid 301 away from the fluid flow path 64 or a portion thereof.

Figure 22:
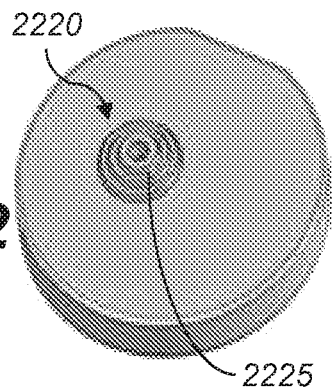

FIG. 22 is a bottom perspective view of components of a lateral-flow assay device according to various aspects. In the illustrated configuration, a nozzle 2220 has a stepped surface 2225 facing the substrate 9, FIG. 19. This advantageously provides defined locations at which menisci will preferentially form, e.g., the edges of the steps.

Figure 23:
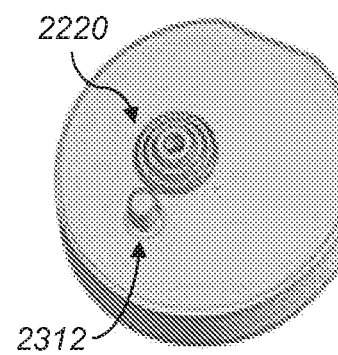

FIG. 23 is a bottom perspective view of components of a lateral-flow assay device according to various aspects. In the illustrated configuration, at least one of the flow constrictions 310 is a protrusion 2312 is spaced apart from the nozzle 2220. The protrusion 2312 can attract excess volumes of the wash fluid 301, e.g., as described above with reference to FIG. 21.

FIGS. 24-27 are bottom perspective views of respective covers 990 of various exemplary lateral-flow assay devices. Each of the covers 990 includes the respective hydrophilic surface 908.

Figure 24:
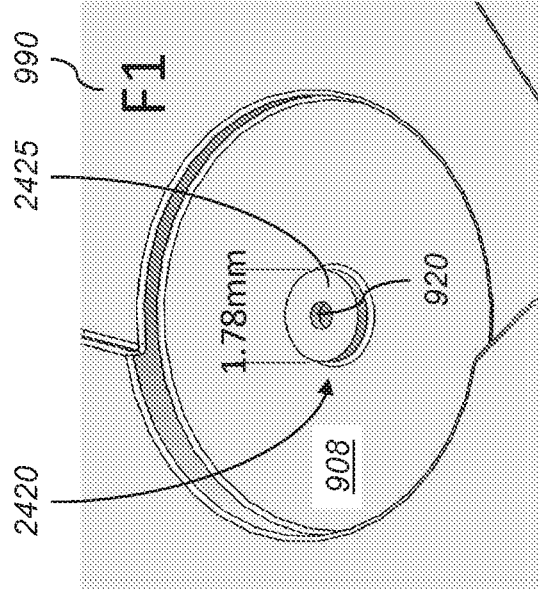

FIG. 24 is a bottom perspective view of components of a lateral-flow assay device according to various aspects. In the illustrated configuration, the nozzle 2420 has a relatively broad plateau 2425 surrounding a relatively narrow aperture 920. The aperture 920 can be broader where the wash fluid 301 is added to the aperture 920, e.g., as shown in FIG. 19. The plateau 2425 is one of the flow constriction(s) 310 in this example. The plateau 2425 can be, e.g., 1.78 mm in diameter.

Figure 25:
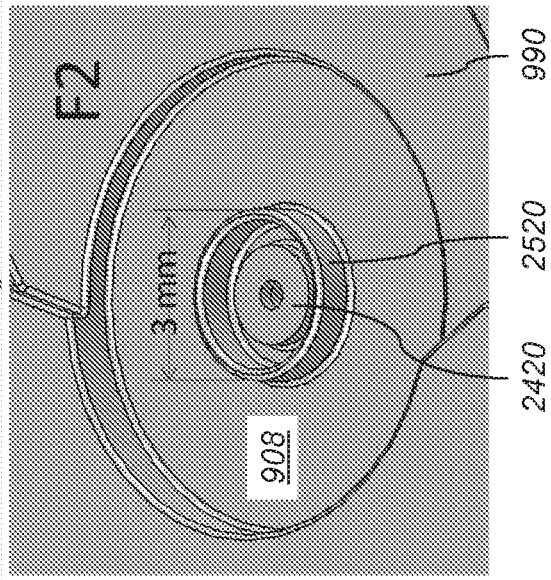

FIG. 25 is a bottom perspective view of components of a lateral-flow assay device according to various aspects. In the illustrated configuration, similar to the configuration shown in FIG. 18, at least one of the flow constriction(s) 320 includes an annulus 2520 arranged around the nozzle 2420 and extending a larger distance from the cover 990 than does the nozzle 2420. In this example, the outside diameter of the annulus 2520 is 3 mm. The annulus 2520 can be concentric with the nozzle 2420, or can be axially offset therefrom. The relative positions of the annulus 2520 and the nozzle 2420 can be selected to provide desired shapes of the menisci that form when the wash fluid 301 is added to the lateral-flow assay device.

Figure 26:
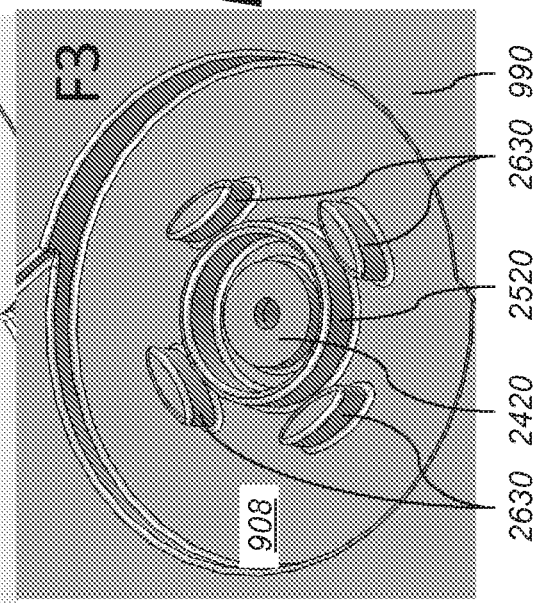

FIG. 26 is a bottom perspective view of components of a lateral-flow assay device according to various aspects. In the illustrated configuration, at least one of the flow constriction(s) 310 includes a plurality of protrusions 2630 arranged substantially symmetrically about the annulus 2520 and spaced apart from the annulus 2520. In this example, four of the protrusions 2630 are present, spaced at 90° intervals around the annulus 2520. The annulus 2520, the nozzle 2420, and the protrusions 2630 can have any desired relationship of relative height off the cover 990. As described above with reference to FIG. 21, the protrusions 2630 provide increased control of where excess volumes of the wash fluid 301 are stored. In various aspects, the protrusions 2630 can all have the same shape or can have any number of different shapes; any number of the protrusions 2630 can be used; and the protrusions 2630 can be spaced at any angles, evenly or unevenly.

Figure 27:
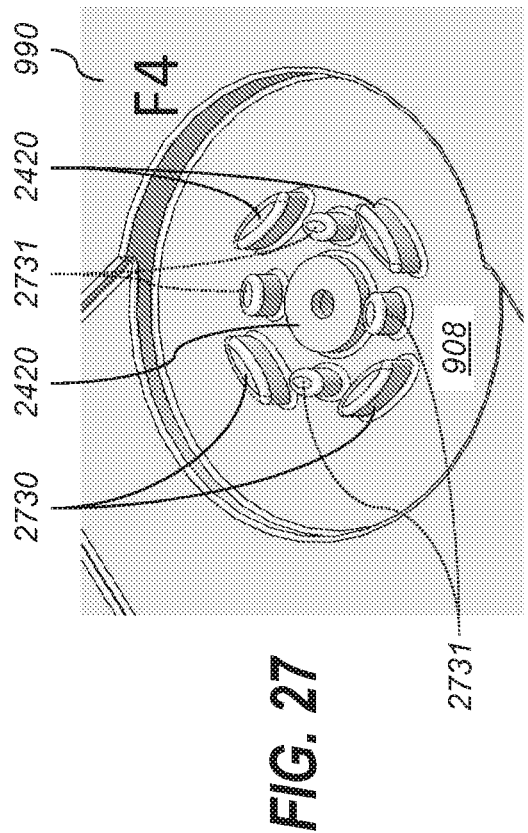

FIG. 27 is a bottom perspective view of components of a lateral-flow assay device according to various aspects. In the illustrated configuration, at least one of the flow constriction(s) 310 includes a plurality of protrusions 2730, 2731 arranged substantially symmetrically about the nozzle 2420 and spaced apart from the nozzle 2420. In this example, four of the protrusions 2730 are arranged alternating with four of the protrusions 2731 around the nozzle 2420 at 45° intervals. Solid and dotted lead lines are used for clarity only and without limitation. In various aspects, the protrusions 2730, 2731 can all have the same shape or can have any number of different shapes; any number of the protrusions 2730, 2731 can be used; and the protrusions 2730, 2731 can be spaced at any angles, evenly or unevenly.

The configurations shown in FIGS. 26 and 27 can be useful for lateral-flow assay devices using high volumes of the wash fluid 301 compared to, e.g., the configurations shown in FIGS. 24 and 25.

FIGS. 28-36 are graphical representations of photographs of stages in experimental tests of an exemplary lateral-flow assay device according to various aspects. The tested exemplary lateral-flow assay device was configured as shown in FIGS. 11A-11B.

Experiment 1 (FIGS. 28-30), experiment 2 (FIGS. 31-33), and experiment 3 (FIGS. 34-36) illustrate that various flow constriction(s) 310 can, together with the hydrophilic surfaces 308, 908, effectively deliver different wash fluids (water, POC wash and NDSB Wash) to accomplish wash effectively and maintain the stability of wash fluid menisci within the wash addition area 409 in the lateral-flow assay device during an assay fluid flow process. The properties of the tested wash fluids 301 are listed in Table 3:

TABLE 3

| Wash Fluid | Viscosity (cP) | Surface Tension (dynes/cm) |
|---|---|---|
| DI Water | 0.88 | 72.7 |
| POC Wash 1.0 | 0.93 | 32.8 |
| NDSB (FlumAb) | 0.92 | 31.9 |

Figures 28, 29, 30:
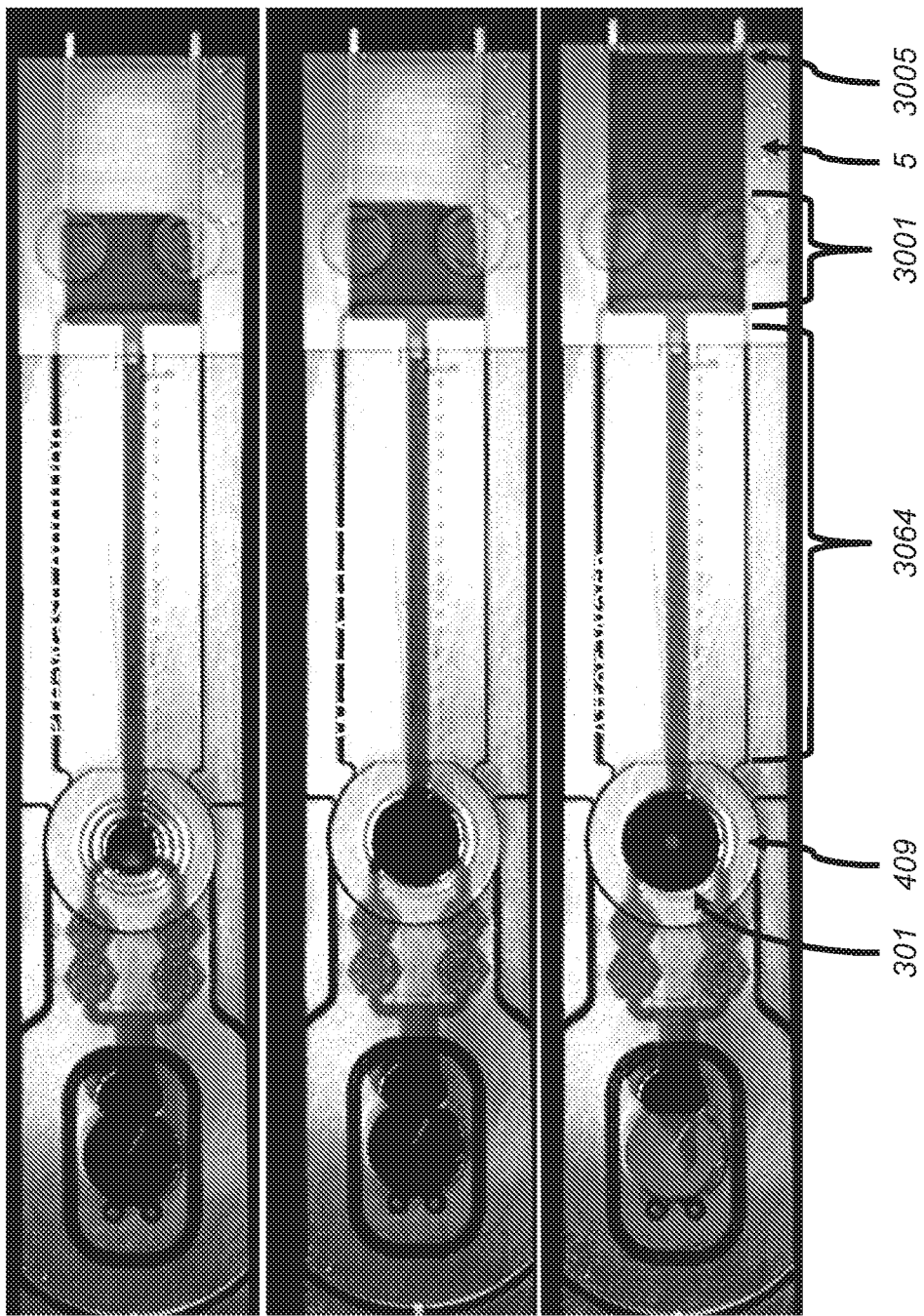
FIGS. 28-30 are graphical representations of photographs of stages in an experimental test of an exemplary lateral-flow assay device according to various aspects.

Referring to FIGS. 28-30, there are shown stages in Experiment 1. The sample 101, FIG. 1, was 1% silwet surfactant in plasma and included red food dye for visibility. Eight microliters of the sample 101 were added to the sample addition zone 2, FIG. 1. Once the sample 101 filled about 40% of the volume of the wicking zone 5, FIG. 1, 17 μL of POC wash fluid (at room temperature) with blue food dye was added to the wash addition zone 409. Red food dye is added to the sample, and blue dye is added to the wash fluid, FIGS. 28-30 show fluid flow and wash patterns at three different stages of the tested assay process with wash addition.

FIG. 28 shows the sample 101 (red color) having filled about 40% of the volume of the wicking zone 5 prior to wash addition. FIG. 28 shows the tested lateral-flow assay device immediately after adding the wash fluid 301 (blue color). The grooves 410, FIG. 4, are retaining the wash fluid 301. FIG. 30 shows the distribution of the wash fluid 301 distribution when fluid, in this test the sample 101, reaches the end 3005 of the wicking zone 5. In this experiment, the fluid of the sample 101 was completely displaced by the wash fluid in the detection zone channel 3064 of the fluid flow path 64, FIG. 3. Moreover, the wash fluid extended into the wicking zone 5 in a region 3001. The fluid under the wash addition zone 409 is still pinned within the grooves 410 and is still stable after the wash flow is complete.

Referring to FIGS. 31-33, there are shown stages in Experiment 2. The sample 101 as in Experiment 1 was added to the sample addition zone 2. FIG. 31 shows the sample 101 (red color) having filled about 30% of the volume of the wicking zone 5 prior to wash addition. At that point, the wash fluid 301 was added. FIG. 32 shows the tested lateral-flow assay device immediately after adding the wash fluid 301, in this experiment 17 μL de-ionized water (at room temperature) plus green food dye (green color). The wash fluid 301 (green color) is retained within the grooves 410. FIG. 33 shows the lateral-flow assay device When fluid, in this instance the sample 101, reached the end 3005 of the wicking zone 5. The fluid of the sample 101 (red color) is completely displaced by the wash fluid 301 (green color) in the detection zone channel 3064. Moreover, the wash fluid extended into the wicking zone 5 in a region 3301. The wash fluid 301 in the wash addition zone 409 is still pinned within the grooves 410 and is still stable after the wash flow is complete.

Figures 34, 35, 36:
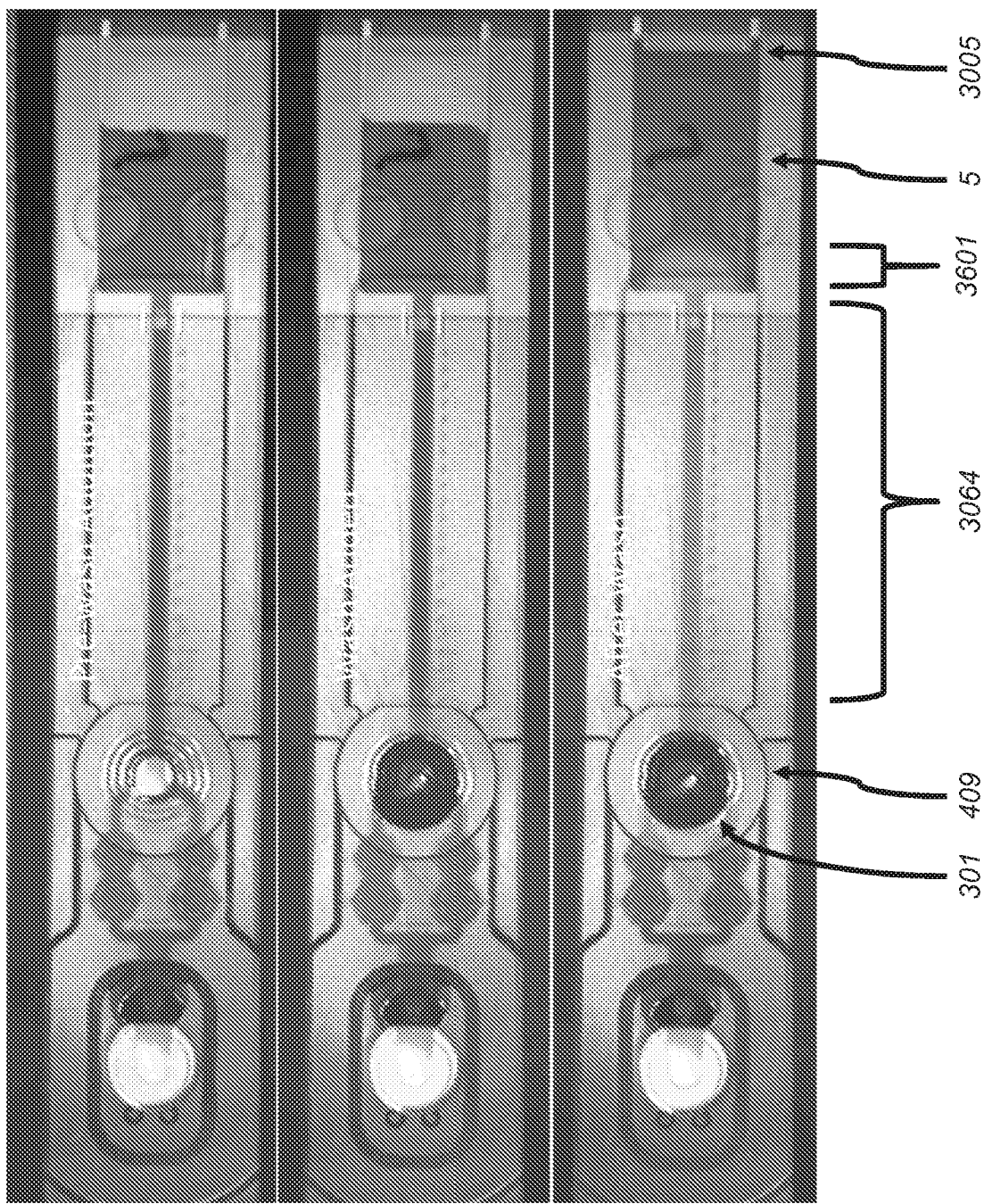
FIGS. 34-36 are graphical representations of photographs of stages in yet another experimental test of an exemplary lateral-flow assay device according to various aspects.

Referring to FIGS. 34-36, there are shown stages in Experiment 3. The sample 101 as in Experiment 1 was added to the sample addition zone 2. FIG. 34 shows the sample 101 (red color) having filled about 60% of the volume of the wicking zone 5 prior to wash addition. At that point, the wash fluid 301 was added. FIG. 35 shows the tested lateral-flow assay device immediately after adding the wash fluid 301, in this experiment 17 μL NDSB Wash fluid (at room temperature) plus blue food dye (blue color). The wash fluid 301 (blue color) is retained within the grooves 410, FIG. 4. FIG. 36 shows the lateral-flow assay device when fluid, in this instance the sample 101, reached the end 3005 of the wicking zone 5. The fluid of the sample 101 (red color) is completely displaced by the wash fluid 301 (blue color) in the detection zone channel 3064. Moreover, the wash fluid extended into the wicking zone 5 in a region 3601. The wash fluid 301 in the wash addition zone 409 is still pinned within the grooves 410 and is still stable after the wash flow is complete.

Various experiments were conducted for the configurations shown in FIGS. 24-27 using POC wash fluid. For all four of those tested configurations, wash was performed effectively for all three tested dispense volumes (10, 15 and 20 μL) of the POC wash fluid 301. The wash fluid 301 was clearly visible in the detection zone channel 3064 and the wicking zone 5. In some configurations, the wash fluid 301 moved only downstream if the sample 101 was not touching the cover 990. In some configurations, the wash fluid moved both upstream and downstream if the sample 101 touched the cover 990. All tested configurations provided stable menisci for volumes of the wash fluid 301 of 10 μL and 15

μL. The wash fluid 301 was retained within the third (outermost) ring of the grooves 410 at those volumes. For a volume of 20 μL, the wash fluid 301 passed the third ring in some tests. In one test, non-stable meniscus behavior was observed, Accordingly, the flow constrictions 310 can be designed based on the volumes of the sample 101 and the wash fluid 301 to provide stable meniscus behavior. In various tested configurations using nubs (e.g., the protrusions 2630, FIG. 26), the nubs did attract the dispensed wash fluid 301. The menisci were not symmetric in every test. Accordingly, the flow constrictions 310 can be designed based on the volumes of the wash fluid 301 and the configuration of the fluid flow path 64 to provide menisci with a desired degree of symmetry.

Figure 37:
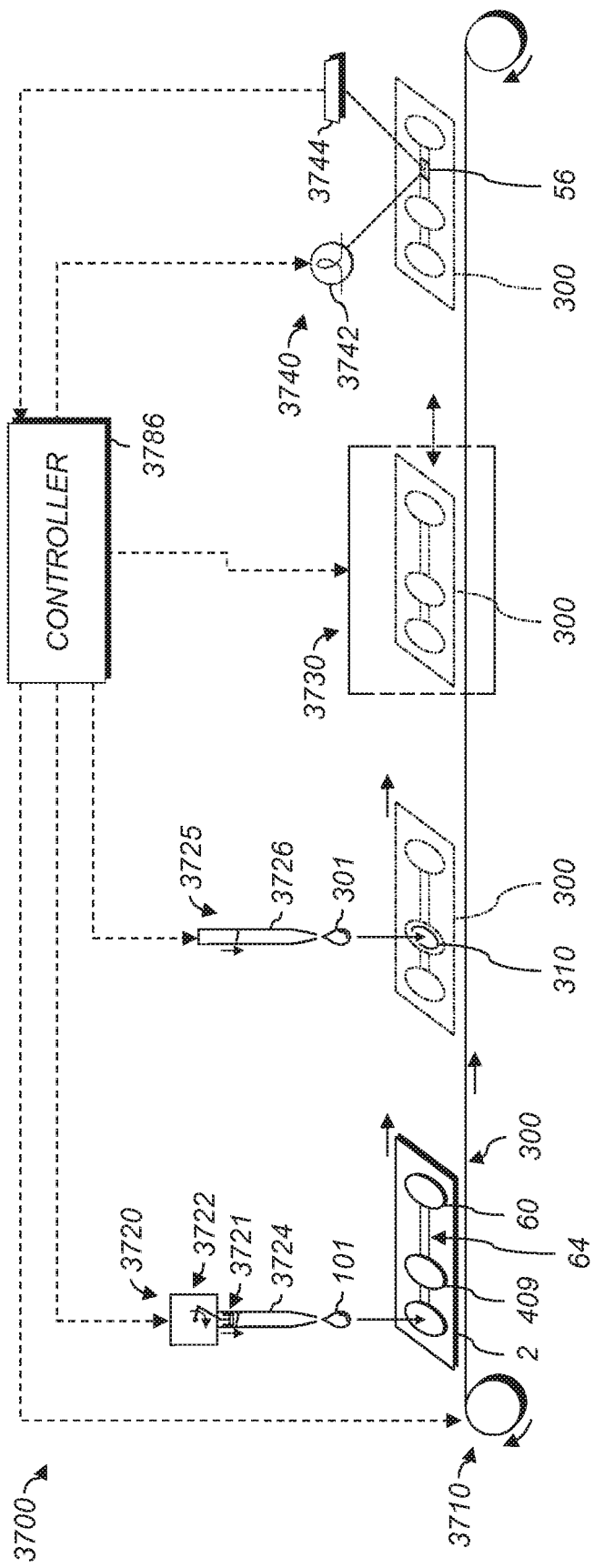
FIG. 37 is a schematic of an apparatus for analyzing a fluidic sample according to at least one exemplary embodiment, and related components.

Referring to FIG. 37, there is shown an apparatus 3700 for analyzing a fluidic sample 101 according to at least one exemplary embodiment. The apparatus 3700 includes a transport system 3710 for conveying the lateral-flow assay device 300 between components described below. For simplicity, the transport system 3710 is represented as a continuous conveyor belt. However, this is not limiting. The transport system 3710 can include conveyor(s), gripper(s), robotic arm(s), or other device(s) for moving the lateral-flow assay device 300 with respect to below-described components, or can include stage(s), conveyor(s), or other device(s) for moving below-described components with respect to the lateral-flow assay device 300, in any combination, Various examples of the transport system 3710 are described in commonly-assigned U.S. Pat. No. 8,080,204 to Ryan et al. and U.S. Pat. No. 8,043,562 to Tomasso et al., each of which is incorporated herein by reference, and in U.S. Pat. No. 7,632,468 to Barski, et al, incorporated herein by reference. Positions of the lateral-flow assay device 300 at various stages of processing are shown in phantom.

In this example, the lateral-flow assay device 300 includes the sample addition zone 2, the wash addition zone 409, and the wicking zone 60 disposed in that order along the fluid flow path 64, e.g., as discussed above with reference to FIG. 3. Any of the above-described embodiments of lateral-flow assay devices can be used in addition to or in place of the lateral-flow assay device 300, e.g., the lateral-flow assay devices 300, 400, 700, 800, 900, 1100, 1200, 1300, 1400, 1900, or other illustrated or described lateral-flow assay devices.

A sample-metering mechanism 3720 is configured to selectively apply the fluidic sample 101 to the sample addition zone 2 of the at least one lateral-flow assay device 300. The illustrated sample-metering mechanism 3720 includes a disposable metering tip 3724 holding, e.g., 250 μL of the fluidic sample 101. In various aspects, there is a one-to-one correspondence between a particular fluidic sample 101 and a particular disposable metering tip 3724. In an example, each metering event meters between ~5 μL and ~10 μL of the fluidic sample 101.

In the illustrated example, and for explanation only, the sample-metering mechanism 3720 includes a piston 3721 and a driving system 3722 operating the piston 3721 to dispense a selected volume of the fluidic sample 101 from the metering tip 3724. Other structures for metering can also be used, e.g., air or fluid pressure sources or piezoelectric or thermal actuators. An exemplary metering tip 3724 is described in. U.S. Publication No. 2004/0072367 by Ding, et al., the disclosure of which is incorporated herein by reference. Metering the sample 101 onto a lateral-flow assay device 100 is referred to herein as "spotting."

The exemplary apparatus 3700 further includes the wash-metering mechanism 3725 configured to selectively apply the wash fluid 301 to the wash addition zone 409 of the lateral-flow assay device 300. In an example, the wash-metering mechanism 3725 includes a metering nozzle 3726 and an actuator (not shown), e.g., a piston such as the piston 3721. In another example, the wash-metering mechanism includes a blister.

The wash addition zone 409 includes one or more flow constriction(s) 310 spaced apart from the fluid flow path 64 to form a meniscus in the applied wash fluid. Examples of the wash addition zones 409 and the flow constrictions 310 are discussed above with reference to FIGS. 3-27. As discussed above, the fluid flow path 64 is configured to draw the applied wash fluid 301 out of a reservoir 535, FIG. 5, defined at least partly by the meniscus.

The exemplary apparatus 3700 includes at least one incubator 3730. Various types of sample testing, including potentiometric, rate chemistry, and endpoint tests, may be required for any given patient sample, necessitating both different incubation intervals and different test apparatus within the incubator 3730. Accordingly, more than one incubator, or a tandem or other multi-test-capable incubator can be used. For clarity, only one incubator 3730 is shown. Various examples of the incubators 3730 and related components are described in U.S. Pat. Nos. 4,287,155 and 7,312,084 to Jakubowicz, et al., entitled "Tandem Incubator for Clinical Analyzer," each of which is hereby incorporated by reference in its entirety.

The incubator 3730 retains the lateral-flow assay device(s) 300, e.g., at room temperature or under selected environmental conditions, until an accurate measurement can be taken. Some lateral-flow assay devices 300 require endpoint testing, which requires only a single read be performed following a predetermined incubation interval (e.g., approximately 5 minutes). Other lateral-flow assay devices 300, such as those requiring rate chemistries, require a number of reads to be taken throughout the course of incubation. The incubator 3730 or the transport system 3710 can therefore include structures for transporting lateral-flow assay device(s) 300 between the incubator 3730 and a measurement device 3740, discussed below.

The exemplary apparatus 3700 shown further includes at least one measurement device 3740. The measurement device 3740 can include a potentiometric sensor, e.g., a voltmeter, ammeter, or charge meter, or a colorimetric or other photometric sensor. Exemplary photometric sensors include photodiodes and line-scan or area-scan reflectometers or imagers, e.g., charge-coupled device (CCD) or complementary metal-oxide-semiconductor (CMOS) imagers. Colorimetric sensors can operate in reflective or transmissive modes. Reflective colorimetric sensors can be arranged to measure the front or back of the lateral-flow assay device 300.

In an example, the measurement device 3740 includes a light source 3742 (represented graphically as a lamp). The light source 3742 can include a lamp, light-emitting diode (LED), laser, or other source of optical radiation. The exemplary measurement device 3740 also includes a photosensor 3744 that captures light of the light source 3742 reflected from the detection zone 56 of the lateral-flow assay device 300.

The exemplary apparatus 3700 further includes controller 3786 configured to operate each of the sample-metering mechanism 3720, the wash-metering mechanism 3725, and the at least one measurement device 3740 in accordance with a predetermined timing protocol in order to determine at least one characteristic of the applied fluidic sample 101. The controller 3786 is configured to operate the wash-metering mechanism 3725 after operating the sample-metering mechanism 3720. The controller 3786 can also be configured to operate the incubator 3730.

For clarity only, communications connections between the controller 3786 and other components are shown dashed. Further and according to this exemplary embodiment, the controller 3786 is configured to operate the transport system 3710. For example, the controller 3786 can sequence the motion of the lateral-flow assay device 300 through the sample-metering mechanism 3720, the incubator 3730, and the at least one measurement device 3740 to perform a potentiometric or colorimetric measurement of the fluidic sample 101. The exemplary controller 3786 can be further configured to receive data from the photosensor 3744 and provide a graphical representation of the measured data via an electronic display. The controller 3786 can include various components discussed below with reference to FIG. 39, e.g., a processor 3986.

Figure 38:
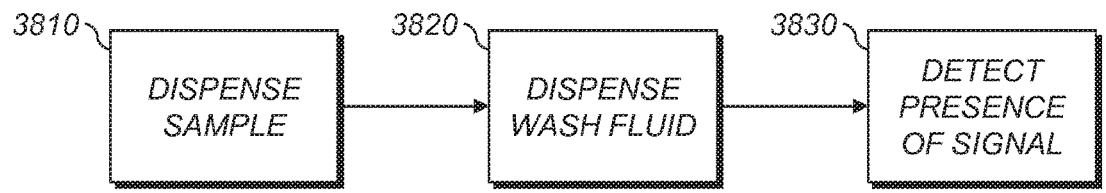
FIG. 38 shows a flowchart illustrating an exemplary method for displacing a fluidic sample in a fluid flow path of an assay device.

FIG. 38 shows a flowchart illustrating an exemplary method for displacing a fluidic sample in a fluid flow path of an assay device. In at least one example, processing begins with step 3810. For clarity of explanation, reference is herein made to various components shown in FIGS. 1-27, 37 that can carry out or participate in the steps of the exemplary method. It should be noted, however, that other components can be used; that is, exemplary method(s) shown in FIG. 38 are not limited to being carried out by the identified components. The method can include automatically carrying out the listed steps using a processor, e.g., the processor 3986, FIG. 39, or another processor in the controller 3786, FIG. 37.

In step 3810, the fluidic sample 101 is dispensed from a sample supply, e.g., the sample-metering mechanism 3720, FIG. 37, onto a sample addition zone 2 of the lateral-flow assay device 300. The dispensed fluidic sample 101 travels along the fluid flow path 64 of the lateral-flow assay device 300.

In step 3820, a wash fluid 301 is dispensed from a wash-fluid supply, e.g., the wash-metering mechanism 3725, FIG. 37, onto a wash addition zone 409 of the lateral-flow assay device 300 downstream of the sample addition zone 2 along the fluid flow path 64. A meniscus is then formed in the dispensed wash fluid 301 by at least one flow constriction 310 of the lateral-flow assay device 300. The fluid flow path 64 draws at least some of the dispensed wash fluid 301 out of the reservoir 535 defined at least partly by the meniscus. The drawn at least some of the dispensed wash fluid 301 displaces at least some of the fluidic sample 101 in the fluid flow path 64. This is discussed above with reference to FIG. 6. Step 3820 permits performing assays that require washing with other than fluid of the sample 101 in order to provide accurate results. In various embodiments, step 3820 is followed by step 3830.

In step 3830, after said dispensing the wash fluid in step 3820, the presence of a detectable signal corresponding to a characteristic of the dispensed fluid sample 101 is determined. This can be done using the incubator 3730, the measurement device 3740, or both. In embodiments using incubation, the incubation time can be selected as appropriate based on the fluidics and dimensions of the lateral-flow assay device 300 and the viscosities or surface tensions of the sample 101 or the wash fluid 301.

Figure 39:
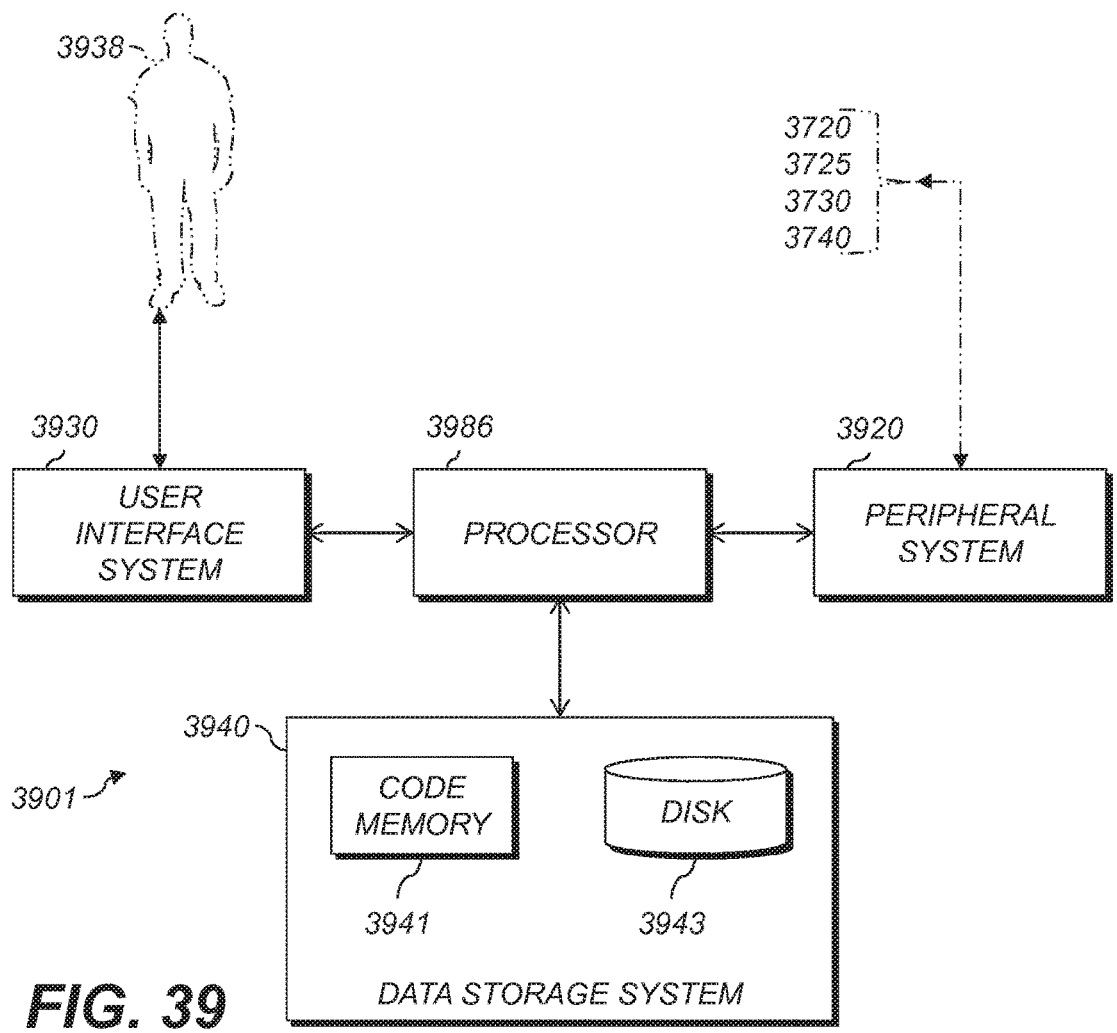
FIG. 39 is a high-level diagram showing components of a data-processing system in accordance with various embodiments.

FIG. 39 is a high-level diagram showing the components of an exemplary data-processing system 3901 for analyzing data, operating an apparatus 3700, FIG. 37, for analyzing samples 101 and performing other analyses described herein, and related components. The data-processing system 3901 includes a processor 3986, a peripheral system 3920, a user interface system 3930, and a data storage system 3940. The peripheral system 3920, the user interface system 3930 and the data storage system 3940 are communicatively connected to the processor 3986. The processor 3986 can be communicatively connected to a network (not shown). The following devices can each include one or more of the systems 3986, 3920, 3930, 3940, and can each connect to one or more network(s): the controller 3786, the sample-metering mechanism 3720, the wash-metering mechanism 3725, the incubator 3730, the light source 3742, and the photosensor 3744, all FIG. 37. The processor 3986, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALS), or digital signal processors (DSPs).

The processor 3986 can implement processes of various aspects described herein. The processor 3986 and related components can, e.g., carry out processes for performing assays or for displacing a fluidic sample 101 in a fluid flow path 64 of a lateral-flow assay device 300. Examples of such processes are described above with reference to FIGS. 37 and 38.

The processor 3986 can be embodied in one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as the peripheral system 3920, the user interface system 3930, and the data storage system 3940 are shown separately from the processor 3986 but can be stored completely or partially within the processor 3986.

The peripheral system 3920 can include one or more devices configured to provide digital content records to the processor 3986. For example, the peripheral system 3920 can include or communicate with one or more measurement device(s) 3740, FIG. 37. The processor 3986, upon receipt of digital content records from a device in the peripheral system 3920, can store such digital content records in the data storage system 3940. In various examples, the peripheral system 3920 is communicatively connected to one or more of the sample-metering mechanism 3720, the wash-metering mechanism 3725, the incubator 3730, the light source 3742, and the photosensor 3744, all FIG. 37.

The user interface system 3930 can convey information in either direction, or in both directions, between a user 3938 and the processor 3986 or other components of the data-processing system 3901. The user interface system 3930 can include a mouse, a keyboard, another computer (connected, e.g., via a network or a null-modem cable), or any device or combination of devices from which data is input to the processor 3986. The user interface system 3930 also can include a display device, e.g., an electronic display 3935, a processor-accessible memory, or any device or combination of devices to which data is output by the processor 3986. The user interface system 3930 and the data storage system 3940 can share a processor-accessible memory.

The data storage system 3940 can include or be communicatively connected with one or more processor-accessible memories configured to store information. The memories can be, e.g., within a chassis or as parts of a distributed system. The phrase "processor-accessible memory" is intended to include any data storage device to or from which the processor 3986 can transfer data (using appropriate components of the peripheral system 3920), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 3940 can be a tangible non-transitory computer-readable storage medium, i.e., a non-transitory device or article of manufacture that participates in storing instructions that can be provided to the processor 3986 for execution.

In an example, the data storage system 3940 includes a code memory 3941, e.g., a RAM, and a disk 3943, e.g., a tangible computer-readable storage device such as a hard drive or Flash drive. Computer program instructions are read into the code memory 3941 from the disk 3943. The processor 3986 then executes one or more sequences of the computer program instructions loaded into the code memory 3941, as a result performing process steps described herein. In this way, the processor 3986 carries out a computer implemented process. For example, steps of methods described herein, blocks of the flowchart illustrations or block diagrams herein (e.g., FIG. 38), and combinations of those, can be implemented by computer program instructions. The code memory 3941 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into the processor 3986 (and possibly also other processors), to cause functions, acts, or operational steps of various aspects herein to be performed by the processor 3986 (or other processor). Computer program code for carrying out operations for various aspects described herein may be written in any combination of one or more programming language(s), and can be loaded from the disk 3943 into the code memory 3941 for execution.

Various above-described embodiments advantageously use flow constriction(s) 310, FIG. 3, in the wash addition zone 409 to stabilize the dispensed wash fluid 301, e.g., to pin the wash fluid 301 to selected locations in the wash addition zone 409. The flow constriction(s) 310 advantageously encourage the formation of one or more partly-meniscus-delimited reservoir(s) 535 that can receive variable volumes of the wash fluid 301 with reduced sensitivity to the dispensing rate of the wash fluid 301. Moreover, the pressure of such menisci is close to the ambient, reducing the probability of overflowing the fluid flow path 64.

Various exemplary flow constriction(s) include nozzle(s) that connects a wash fluid supply to the fluid flow path 64 in the lateral-flow assay device in the wash addition zone 409; very low nozzle outlets to promote contact between the wash fluid 301 in the nozzle and the hydrophilic surface 308 on the substrate 9; and steps outside the nozzle (e.g., as in FIG. 22) to permit variable fluid meniscus sizes (volumes of the reservoir 535) while maintaining meniscus stability.

Various aspects advantageously permit variable-rate, variable-amount delivery of the wash fluid 301, and stabilize the received wash fluid 301 at a desired location. Various aspects reduce the probability of overflowing the fluid flow path 64, which improves wash efficiency. Various aspects advantageously provide robust wash performance with respect to one or more of the following properties:

- Variation in the volume of the wash fluid 301 delivered to the wash addition zone 409 within the range, e.g., from 7 μL to 17 μL. This relaxed volume range can reduce the development cost of wash fluid delivery system (e.g., the blister).
- Variation in the delivery rate of the wash fluid 301 within the range, e.g., 1 μL/sec to >10 μL/sec. This relaxed range also facilitates more effective fluid delivery system design (e.g., a burst of wash fluid from a squeezed blister can be used).
- Maintenance of a stable meniscus in the wash addition zone, independent of above-noted variations in the delivery volume and delivery rate of the wash fluid 301.
- Entry of the wash fluid 301 into the fluid flow path 64 at an appropriate location to effectively displace the fluid of the sample 101 in the fluid flow path 64 without "overflow," i.e., the wash fluid 301 flowing over the sample 101 between the microposts 7 inside the fluid flow path 64.
- Termination of the fluid flow of the sample 101 when the wash fluid 301 is added. Various aspects restrict the sample 101 from flowing along the fluid flow path 64 downstream past the wash addition zone 409 once the wash fluid 301 is added.
- Maintenance of meniscus stability in the wash addition zone 409 as the wash fluid 301 enters the fluid flow path 64 to perform the wash.
- Variation in the amount of the wash fluid 301 to be delivered through the detection zone channel 3064 in the range from 1 μL to 4 □L, or in the range of >4 μL.

Parts List For FIGS. 1-39

1 lateral-flow assay device
2 sample addition zone
3 reagent zone
4 detection zone
5 wicking zone
7 microposts
9 substrate
20 lateral-flow assay device
40 substrate
44 top surface
48 sample addition zone
52 reagent zone
55 detection channel.
56 detection zone
57 flow promoter
60 wicking zone
64 fluid flow path 70 hydrophilic layer
72 vents
100 lateral-flow assay device
101 sample
300 lateral-flow assay device
301 wash fluid
308 hydrophilic surface
310 flow constriction
311 protrusion
400 lateral-flow assay device
409 wash addition zone
410 groove
411 arcuate path
464 centerline
511 corner
520 meniscus
521 angle
530 meniscus
531 angle
535 reservoir
655 area
700 lateral-flow assay device
710 reference point
764 centerline
800 lateral-flow assay device
810 grooves
869 spiral path
900 lateral-flow assay device
908 hydrophilic surface
910 cover flow constriction
911 protrusion
912 cover flow constriction
913 protrusion
920 aperture
930 wash port
935 meniscus
990 cover
1018 proximal edge
1019 distal edge
1035 meniscus
1100 lateral-flow assay device
1120 nozzle
1200 lateral-flow assay device
1210, 1211, 1212, 1213 grooves
1235, 1237 menisci
1300 lateral-flow assay device
1335 meniscus
1400 lateral-flow assay device
1411 lip
1420 distal surface
1435, 1436 menisci
1710, 1810 annuli
1900 lateral-flow assay device
1911 lip
1920 aperture
1995 offset
2112 protrusion.
2220 nozzle
2225 stepped surface
2312 protrusion
2420 nozzle
2425 plateau
2520 annulus
2630, 2730, 2731 protrusions
3001 region
3005 end
3064 detection zone channel
3301, 3601 regions
3700 apparatus
3710 transport system
3720 sample-metering mechanism
3721 piston
3722 driving system
3724 disposable metering tip
3725 wash-metering mechanism
3726 metering nozzle
3730 incubator
3740 measurement device
3742 light source
3744 photosensor
3786 controller
3810, 3820, 3830 steps
3901 data-processing, system
3920 peripheral system
3930 user interface system
3935 electronic display
3938 user
3940 data storage system
3941 code memory
3943 disk
3986 processor
F flow direction The invention is inclusive of combinations of the aspects described herein. References to "a particular embodiment" (or "aspect" or "version") and the like refer to features that are present in at least one aspect of the invention. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. The invention has been described in detail with particular reference to certain preferred aspects thereof, but it will be readily apparent that other modifications and variations are possible within the intended ambits of the concepts described herein and in accordance with the following claims.

The invention claimed is:

1. A method of displacing a fluidic sample in a fluid flow path of an assay device, the method comprising:
dispensing the fluidic sample from a sample supply onto a sample addition zone of the assay device, wherein the dispensed fluidic sample travels along the fluid flow path of the assay device; and
dispensing a wash fluid from a wash-fluid supply onto a wash addition zone of the assay device downstream of the sample addition zone along the fluid flow path so that a meniscus is formed in the dispensed wash fluid by at least one flow constriction of the assay device, wherein the at least one flow constriction is created by substantially circular grooves disposed substantially around the wash addition zone, and wherein the fluid-flow path draws dispensed wash fluid out of a reservoir defined at least partly by the meniscus and the drawn wash fluid displaces at least some of the fluidic sample in the fluid-flow path.

2. The method according to claim 1, further comprising, after said dispensing the wash fluid, determining the presence of a detectable signal corresponding to a characteristic of the dispensed fluid sample.

3. The method of claim 1, which includes determining the presence of the detectable signal at a detection zone of the assay device downstream of the wash addition zone.

4. The method of claim 3, wherein determining the presence of the detectable signal includes using a detection material included within the detection zone, the detection material responsive to an analyte of the fluidic sample.

5. The method according to claim 1, wherein the fluidic sample is configured to flow along the fluid flow path through the wash addition zone via capillary forces.

6. The method according to claim 5, wherein the fluidic sample is configured to flow straight through the wash addition zone.

7. The method according to claim 5, wherein the fluidic sample is configured to curve through the wash addition zone.

8. The method according to claim 1, wherein dispensing the wash fluid includes dispensing the wash fluid onto a hydrophilic surface of the wash addition zone.

9. The method according to claim 1, wherein the wash fluid is configured to spread laterally across the wash addition zone until contacting the at least one flow constriction.

10. The method according to claim 1, which includes incubating the assay device prior to determining a presence of a detectable signal corresponding to a characteristic of the dispensed fluid sample.

* * * * *